(12) United States Patent
Susumu

(10) Patent No.: US 11,154,278 B2
(45) Date of Patent: Oct. 26, 2021

(54) ULTRASOUND SIGNAL PROCESSING DEVICE, ULTRASOUND DIAGNOSTIC DEVICE, AND ULTRASOUND SIGNAL PROCESSING METHOD FOR CALCULATING BLOOD FLOW AND TISSUE INFORMATION

(71) Applicant: Konica Minolta, Inc., Tokyo (JP)

(72) Inventor: Yasuaki Susumu, Osaka (JP)

(73) Assignee: KONICA MINOLTA, INC., Tokyo (JP)

( * ) Notice: Subject to any disclaimer, the term of this patent is extended or adjusted under 35 U.S.C. 154(b) by 368 days.

(21) Appl. No.: 16/190,683

(22) Filed: Nov. 14, 2018

(65) Prior Publication Data

US 2019/0150897 A1 May 23, 2019

(30) Foreign Application Priority Data

Nov. 20, 2017 (JP) .............................. JP2017-223157

(51) Int. Cl.
*A61B 8/06* (2006.01)
*G01S 15/89* (2006.01)
*A61B 8/08* (2006.01)

(52) U.S. Cl.
CPC .............. *A61B 8/5276* (2013.01); *A61B 8/06* (2013.01); *A61B 8/488* (2013.01); *A61B 8/5207* (2013.01);
(Continued)

(58) Field of Classification Search
CPC ....... A61B 8/5276; A61B 8/5207; A61B 8/06; A61B 8/488; G01S 15/8988; G01S 15/8981
See application file for complete search history.

(56) References Cited

U.S. PATENT DOCUMENTS 5,669,385 A * 9/1997 Pesque ................ G01S 15/8981
600/453
10,537,310 B2 * 1/2020 Tanaka ..................... A61B 8/06
(Continued)

FOREIGN PATENT DOCUMENTS

| JP | 2014158698 A | 9/2014 |
| JP | 2015-142608 A | 8/2015 |

(Continued)

OTHER PUBLICATIONS

JPO, Notice of Reasons for Refusal for corresponding Japanese patent application No. 2017-223157, dated Jun. 8, 2021, with English translation.

*Primary Examiner* — Serkan Akar
*Assistant Examiner* — Nicholas A Robinson
(74) *Attorney, Agent, or Firm* — Lucas & Mercanti, LLP

(57) ABSTRACT

An ultrasound signal processing device that generates, for each detection wave, a first complex Doppler signal sequence through quadrature detection of a reception signal sequence; generates tissue velocity data by calculating velocity values for each set of coordinates of observation points in a region of interest from the first complex Doppler signal sequence; generates a second complex Doppler signal sequence by performing clutter removal filter processing on the first complex Doppler signal sequence; generates first velocity data by calculating velocity values for each set of coordinates of the observation points from the second complex Doppler signal sequence; and generates, for each set of coordinates of the observation points, second velocity data based on the first velocity data and the tissue velocity data, and third velocity data by applying a correction to velocity values of the second velocity data that have an absolute value equal to or less than a threshold.

12 Claims, 15 Drawing Sheets

(52) U.S. Cl.
CPC ...... *G01S 15/8981* (2013.01); *G01S 15/8988* (2013.01)

(56) References Cited

U.S. PATENT DOCUMENTS

| | | | |
|---|---|---|---|
| 10,820,890 B2* | 11/2020 | Palti | G16H 50/30 |
| 2012/0130249 A1* | 5/2012 | Lee | G01N 29/0654 |
| | | | 600/454 |
| 2015/0359507 A1* | 12/2015 | Shibata | A61B 8/5207 |
| | | | 600/443 |
| 2016/0361040 A1* | 12/2016 | Tanaka | A61B 8/5246 |
| 2017/0071577 A1* | 3/2017 | Seo | G01S 7/52071 |

FOREIGN PATENT DOCUMENTS

| | | | | |
|---|---|---|---|---|
| JP | 2015198710 A | 11/2015 | | |
| JP | 2016-135187 A | 7/2016 | | |
| WO | 2012137431 A1 | 11/2012 | | |
| WO | WO-2018058606 A1 * | 4/2018 | ............... | A61B 8/06 |

* cited by examiner

ULTRASOUND SIGNAL PROCESSING DEVICE, ULTRASOUND DIAGNOSTIC DEVICE, AND ULTRASOUND SIGNAL PROCESSING METHOD FOR CALCULATING BLOOD FLOW AND TISSUE INFORMATION

This application claims priority to Japanese Patent Application No. 2017-223157, filed Nov. 20, 2017, the contents of which are hereby incorporated by reference in their entirety.

BACKGROUND OF THE DISCLOSURE

Technical Field

The present disclosure relates to ultrasound signal processing devices, ultrasound diagnostic devices, and ultrasound signal processing methods, and in particular to reception beamforming processing in ultrasound signal processing devices that use color flow mapping and to color flow mapping operation processing.

Description of the Related Art

The ultrasound diagnostic device transmits ultrasound to an inside of a subject via an ultrasound probe (hereinafter also referred to as a probe) and receives ultrasound reflected waves (echoes) caused by a difference in acoustic impedance of tissue in the subject. Further, based on an electric signal obtained from reception, an image showing structure of internal tissue of the subject is generated and displayed on a monitor (hereinafter also referred to as a display). Ultrasound diagnostic devices are widely used for morphological diagnoses of living bodies because they are not very invasive and can be used to observe the state of internal tissues in real time via tomographic images and the like.

In recent years, a large number of ultrasound diagnostic devices are being provided with color flow mapping (CFM). In CFM, a Doppler shift (frequency shift) occurring in an echo due to movement of body tissue such as a blood flow is detected, and velocity and power information are displayed as a two-dimensional Doppler image superimposed on a two-dimensional tomographic image (B mode tomographic image).

Typically, in CFM, information obtained from blood flow (hereinafter also referred to as "blood flow information") is imaged. Thus, as a process of extraction of a blood flow information component (hereinafter also referred to as "blood flow component") included in an echo, a moving target indicator (MTI) filter may be used, for example. An MTI uses a difference in average velocity of the blood flow component and a component of information obtained from moving tissue and stationary tissue (hereinafter also referred to as "clutter component") to filter out the clutter component from an echo. Further, a method has been proposed of acquiring information representing movement of a subject based on B mode tomographic image data corresponding to a Doppler image and using the information representing movement of the subject to correct ultrasound Doppler image data in order to remove a clutter component (for example, JP 2015-198710).

SUMMARY

However, in situations such as high probe operation speed or high movement speed of tissue such as an organ, i.e., situations in which probe movement speed relative to tissue is high, frequency shifts of tissue and blood flow are superimposed, and therefore there is a problem that a clutter component cannot be sufficiently removed from a Doppler image. Further, in a method of applying motion correction detected from a B mode tomographic image to a corresponding Doppler image, correction is performed based on echo signals pertaining to different transmission and reception, and therefore there is a technical problem that excessive or insufficient removal of a clutter component may occur.

The present disclosure has been in made in view of at least one of these technical problems, and it is an object of the present disclosure to provide an ultrasound signal processing device that detects velocity of tissue in a Doppler signal and adaptively removes a clutter component caused by motion of the tissue according to the velocity of the tissue, in order to extract a blood flow component with high accuracy.

To achieve at least one of the abovementioned objects, according to an aspect of the present disclosure, an ultrasound signal processing device reflecting one aspect of the present disclosure calculates blood flow information by driving a plurality of transducers arranged in an ultrasound probe to execute ultrasound transmission and reception with respect to a subject, the ultrasound signal processing device including ultrasound signal processing circuitry, the ultrasound signal processing circuitry comprising: a transmitter that transmits, a plurality of times, via the plurality of transducers, detection waves to a region of interest denoting a range to be analyzed in the subject; a reception beamformer that generates, for each of the detection waves, a reception signal sequence based on reflected ultrasound from the subject received in a time sequence by the plurality of transducers; a quadrature detector that generates, for each of the detection waves, a first complex Doppler signal sequence through quadrature detection of the reception signal sequence; a tissue velocity detector that generates tissue velocity value data by calculating velocity values for each set of coordinates of observation points in the region of interest from the first complex Doppler signal sequence; a filter processor that generates a second complex Doppler signal sequence by performing clutter removal filter processing on the first complex Doppler signal sequence; a blood flow calculator that generates first velocity value data by calculating velocity values for each set of coordinates of the observation points from the second complex Doppler signal sequence; an adaptable threshold processor that generates, for each set of coordinates of the observation points, (i) second velocity value data based on the first velocity value data and the tissue velocity value data, and (ii) third velocity value data by applying a correction to velocity values of the second velocity value data that have an absolute value equal to or less than a velocity threshold; and an image generator that generates, for each set of coordinates of the observation points, color Doppler image data based on the third velocity value data.

BRIEF DESCRIPTION OF THE DRAWINGS

These and other objects, advantages, and features provided by one or more embodiments of the disclosure will become more fully understood from the detailed description given hereinbelow and the appended drawings which are given by way of illustration only, and thus are not intended as a definition of the limits of the present invention.

DETAILED DESCRIPTION

Developments Leading to Embodiments

Figure 16:
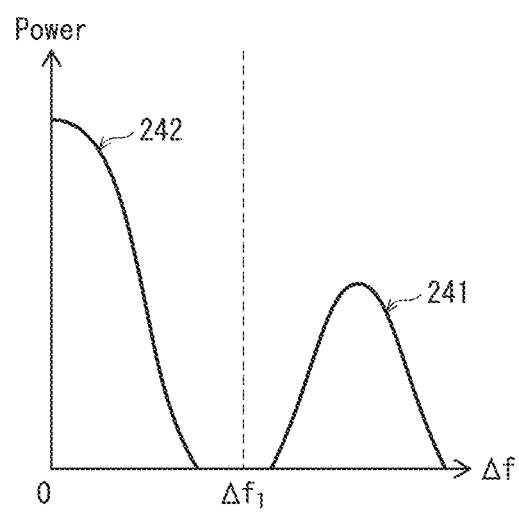
FIG. 16 is a schematic diagram illustrating an example of hands of a blood flow component and a clutter component.

Using an MTI filter, the inventor conducted various studies on how to select signals to be removed. As an MTI filter, a finite impulse response (FIR) filter can be used, which makes use of a difference in average velocity between a blood flow component and a clutter component. A high pass filter such as an FIR filter is a filter that eliminates signals having a frequency lower than a defined cutoff frequency through use of a difference in average velocity between a blood flow component and a clutter component. Such a filter functions effectively when frequency bands of the blood flow components and the clutter component do not overlap. For example, as illustrated in FIG. 16, frequency bands of a blood flow component 241 and a clutter component 242 are separate from each other, and in this case a frequency $\Delta f1$ that is lower than a lowest frequency of the blood flow component 241 and higher than a highest frequency of the clutter component 242 is a cutoff frequency. In this way, the blood flow component 241 passes the FIR filter while the clutter component 242 is removed by the FIR filter, and therefore extraction of only the blood flow component 241 is possible. However, when frequency bands of the blood flow component and the clutter component overlap, an FIR filter cannot be said to be effective. A method described in JP 2015-198710 is a method by which information representing motion of a subject is acquired based on B mode tomographic image data corresponding to a Doppler image or ultrasound reception signals for generating the image data corresponding to the Doppler image, ultrasound Doppler image data is corrected, and a clutter component removed. Accordingly, even if there is an overlap of frequency bands of the blood flow component and the clutter component, the clutter component can be selected and removed.

However, in the method of applying motion correction detected from a B mode tomographic image to a corresponding Doppler image, a correction value for the Doppler image is calculated from a B mode tomographic image based on echo signals pertaining to a different transmission and reception. Thus, in situations such as high probe operation velocity or high movement velocity of tissue such as an organ, i.e., situations in which probe movement velocity relative to tissue is high, excess or deficiency occurs in a size of a clutter components to be removed, and therefore there is a problem that a clutter component cannot be sufficiently removed. In such cases, it may be considered that improvement of Doppler image quality is hindered by the fact that signals that are a basis for correction value determination and signals that are correction targets are acquired in different transmission and reception sequences.

In view of this, the inventor investigated a processing method of detecting a clutter component from a signal based on the same transmission and reception sequence as a Doppler signal to be corrected and adaptively correcting the Doppler signal according to clutter component size in a range in which the clutter component is present in the Doppler signal; and the inventor arrived at embodiments of an ultrasound signal processing device, an ultrasound signal processing method, and an ultrasound diagnostic device using same. [0028]1 The following is a description of embodiments of an ultrasound signal processing device, an ultrasound signal processing method, and an ultrasound signal processing device using same, described with reference to the drawings.

Hereinafter, one or more embodiments of the present disclosure will be described with reference to the drawings. However, the scope of the invention is not limited to the disclosed embodiments.

Embodiment 1

<Overall Configuration>

The following is a description of an ultrasound diagnostic device 100 pertaining to Embodiment 1, described with reference to the drawings.

Figure 1:
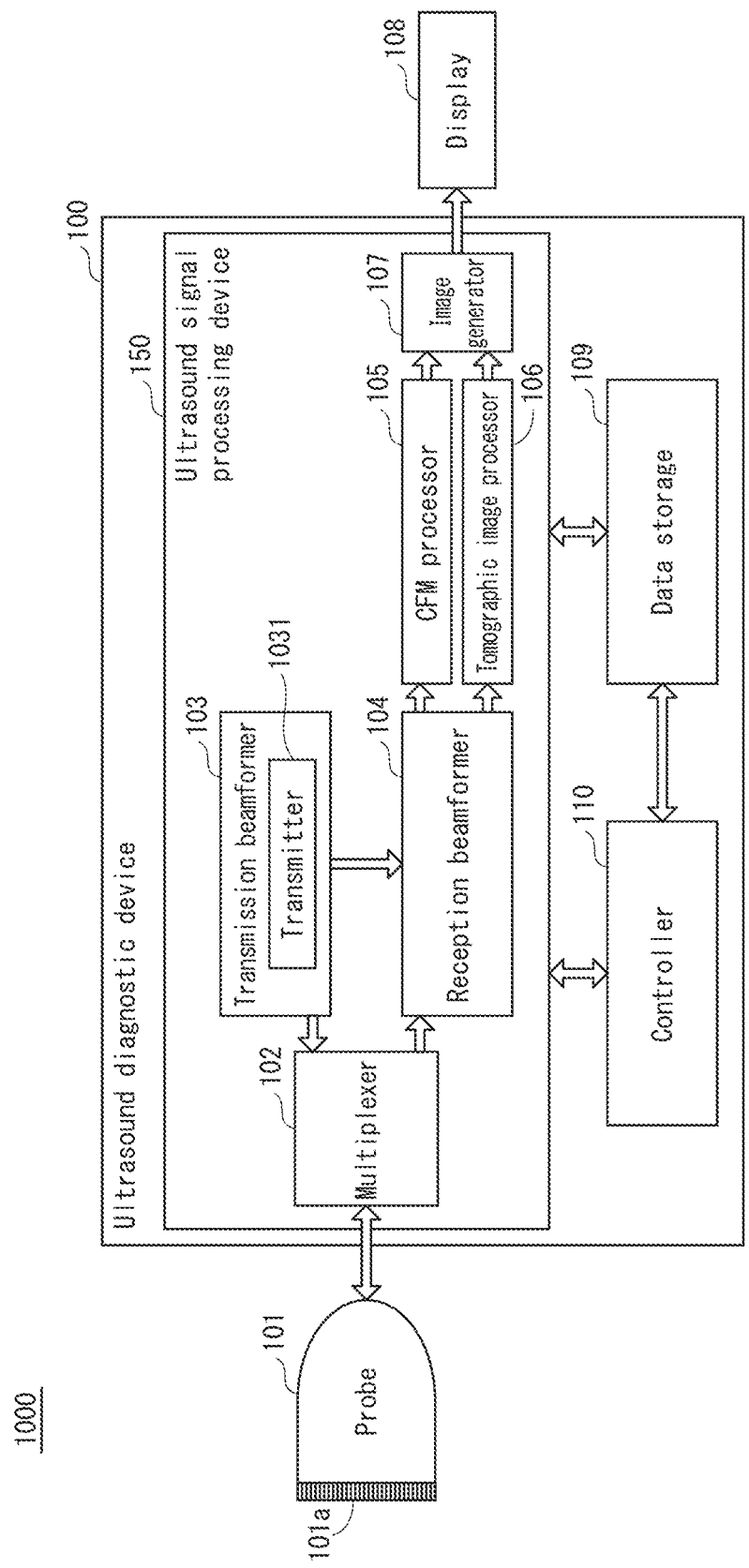
FIG. 1 is a function block diagram of an ultrasound diagnostic system 1000 pertaining to Embodiment 1.

FIG. 1 is a function block diagram of an ultrasound diagnostic system 1000 pertaining to Embodiment 1. In FIG. 1, the ultrasound diagnostic system 1000 includes a probe 101 that has transducers 101*a* that transmit ultrasound towards a subject and receive reflected waves, the ultrasound diagnostic device 100 that causes the probe 101 to transmit and receive ultrasound and generates ultrasound images based on output signals from the probe 101, and a display 108 that displays an ultrasound image on a screen. The probe 101 and the display 108 are each connectable to the ultrasound diagnostic device 100. FIG. 1 illustrates the probe 101 and the display 108 connected to the ultrasound diagnostic device 100. The probe 101 and the display 108 may be incorporated in the ultrasound diagnostic device 100.

<Configuration of Ultrasound Diagnostic Device 100>

The ultrasound diagnostic device 100 includes a multiplexer 102 that selects transducers used for transmission or reception among the transducers 101a of the probe 101 and secures input/output of selected transducers, a transmission beamformer 103 that controls timing of high voltage application to the transducers 101a of the probe 101 in order to perform ultrasound transmission, and a reception beamformer 104 that amplifies and A/D converts electric signals obtained by the transducers 101a based on reflected ultrasound received by the probe 101 in order to generate a reception signal sequence, performs reception beamforming with respect to the reception signal sequence, and generates an acoustic line signal. Further, the ultrasound diagnostic device 100 includes a CFM processor 105 that frequency analyzes an output signal from the reception beamformer 104 to generate color flow information, a tomographic image processor 106 that generates a tomographic image (B mode image) based on an output signal from the reception beamformer 104, an image generator 107 that superimposes color flow information and a B mode image to generate a Doppler image and displays the Doppler image on the display 108, a data storage 109 that stores reception signal sequences and/or acoustic line signals generated by the reception beamformer 104, color flow information generated by the CFM processor 105, and B mode images generated by the tomographic image processor 106, and a controller 110 that controls each element of the ultrasound diagnostic device 100. Of these, the multiplexer 102, the transmission beamformer 103, the reception beamformer 104, the CFM processor 105, the tomographic image processor 106, and the image generator 107 constitute an ultrasound signal processing device 150, which is an ultrasound signal processing circuit.

Elements of the ultrasound diagnostic device 100, for example the multiplexer 120, the transmission beamformer 103, the reception beamformer 104, the CFM processor 105, the tomographic image processor 106, the image generator 107, and the controller 110 are each implemented as a hardware circuit such as a field programmable gate array (FPGA), an application specific integrated circuit (ASIC), or the like.

The data storage 109 is a computer-readable storage medium, and may be a flexible disk, a hard disk, magneto-optical (MO), a digital versatile disc (DVD), digital versatile disc random access memory (DVD-RAM), a Blu-ray Disc (BD), semiconductor memory, or the like. Further, the data storage 100 may be a storage device that is external and connectable to the ultrasound diagnostic device 100.

The ultrasound diagnostic device 100 pertaining to the present embodiment is not limited to the ultrasound diagnostic device configuration illustrated in FIG. 1. For example, the transmission beamformer 103 and the reception beamformer 104 may be directly connected to the transducers 101a of the probe 101 without the multiplexer 102. Further, the transmission beamformer 103, the reception beamformer 104, or a portion thereof may be inside the probe 101. This is not limited only to the ultrasound diagnostic device 100 pertaining to the present embodiment, and the same applies to an ultrasound diagnostic device pertaining to modifications described below.

<Description of Component Elements>

1. Transmission Beamformer 103

The transmission beamformer 103 is connected to the probe 101 via the multiplexer 102 and controls timing of high voltage application to each of a plurality of transducers included in a transmission aperture consisting of a transmission transducer array of all or a plurality of the transducers 101a of the probe 101 for transmitting ultrasound from the probe 101. The transmission beamformer 103 includes a transmitter 1031.

Based on a transmission control signal from the controller 110, the transmitter 1031 performs transmission processing to supply a pulsed transmission signal for causing transducers included in the transmission aperture among the transducers 101a of the probe 101 to transmit an ultrasound beam. The transmitter 1031 includes, for example, a clock generator circuit, a pulse generator circuit, and a delay circuit. A clock generator circuit is a circuit that generates a clock signal for determining transmission timing of an ultrasound beam. A pulse generator circuit is a circuit for generating a pulse signal that drives transducers. A delay circuit is a circuit for setting a delay time for each transducer for ultrasound beam transmission timing, delaying ultrasound beam transmission by the delay time in order to perform ultrasound beamforming. The transmitter 1031 controls transmission timing of each transducer so that the more central a transducer is in the transmission aperture, the more transmission timing is delayed. As a result, a wavefront of an ultrasound transmission wave transmitted from the transducer array in the transmission aperture is focused (converges) at a transmission focal point at a focal depth in a subject. A wavefront converging at a transmission focal point diffuses again and an ultrasound transmission propagates in a subject. The transmission beamformer 103 may perform a control so that ultrasound converges on a region having a wavefront, i.e., a transmission focal region at a transmission focal depth.

After performing transmission of an ultrasound beam a defined number of times, the transmitter 1031 repeats, a defined number of times, a process of shifting the transmission aperture a defined distance in an array direction and transmitting an ultrasound beam a defined number of times, thereby performing ultrasound transmission from all of the transducers 101a of the probe 101. Hereinafter, each transmission of an ultrasound beam may be referred to as a transmission event, and an entire series of ultrasound transmission using the same transmission aperture, composed of a defined number of transmission events, may be referred to as a transmission event set. Here, a "defined number of times" means at least two times, and, for example, from six to twelve times is beneficial. According to the present embodiment, as one example, the defined number of times is set to be ten. In other words, according to the present embodiment, the transmission aperture is shifted every ten ultrasound transmissions. One frame of a signal is received from a plurality of transmission even sets having different transmission apertures from each other.

The transmitter 1031 may transmit a plane wave that is a transmission detection wave propagating in a specific direction transmitted from each transducer of the probe 101 as an ultrasound beam. In this case, all transducers are driven at the same time, or delay processing is performed such that between two adjacent transducers a delay time difference is a defined value. In this case, the transmission aperture does not shift between transmission event sets, and one frame of a signal is received from one transmission event set.

2. Reception Beamformer 104

The reception beamformer 104 amplifies and A/D converts electric signals obtained by a plurality of the transducers 101a based on reflected ultrasound received by the probe 101, converting the electric signal to RF signals, and generates a reception signal sequence that is a time sequence of a plurality of RF signals. Further, the reception beamformer 104 performs reception beamforming with respect to a reception signal sequence to create an acoustic line signal DS. When generating an acoustic line signal DS, reception signals are identified based on ultrasound reflected from observation points in a region of interest in correspondence with a transmission event, delay processing is performed for each reception signal, then summing is performed.

3. CFM Processor 105

Figure 2:
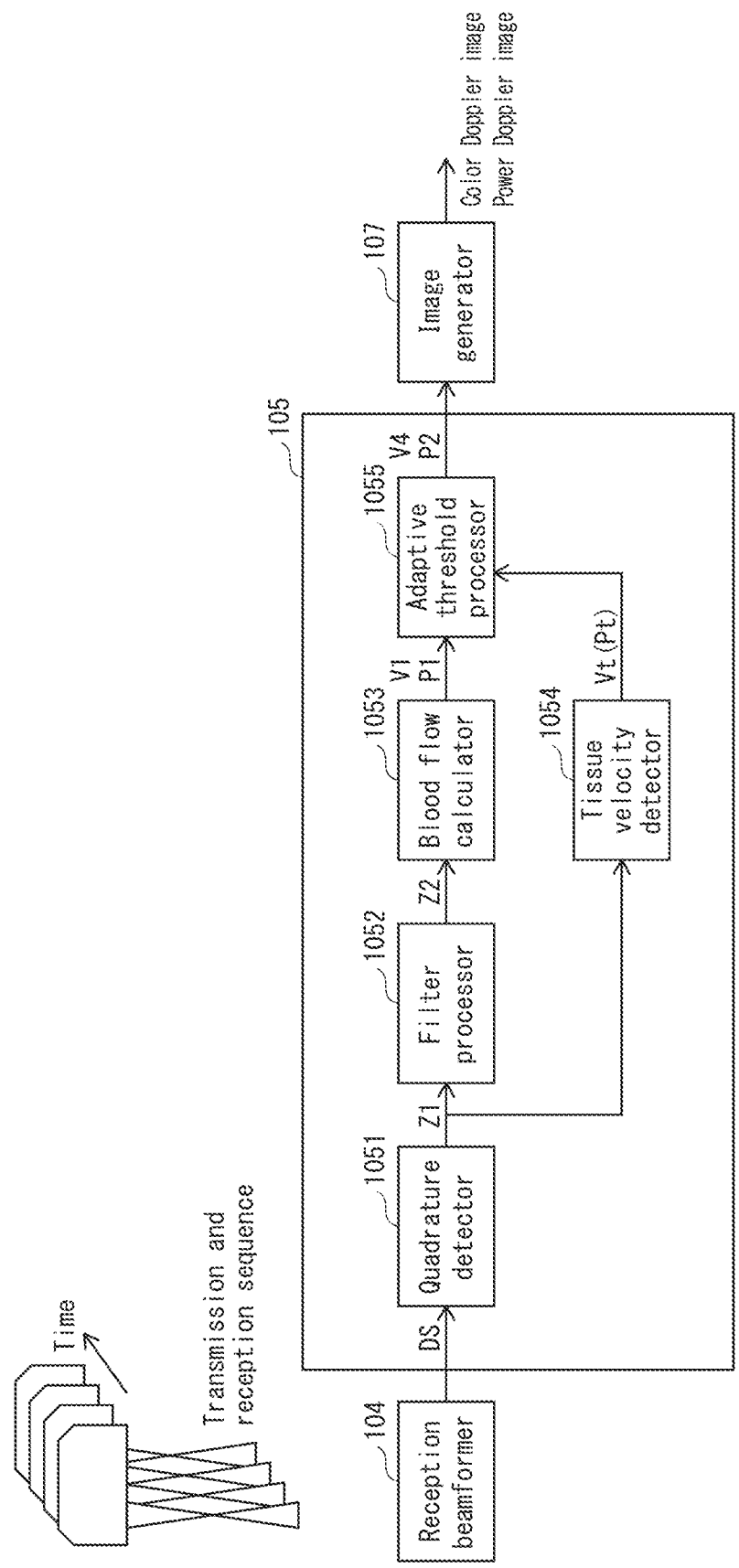
FIG. 2 is a function block diagram of a CFM processor 105.

The CFM processor 105 performs frequency analysis based on acoustic line signal reception signal sequences obtained from transmission event sets, in order to generate CFM signals. The CFM processor 105 may perform frequency analysis based on reception signal sequences obtained from transmission event sets in order to generate CFM signals. Here, for a given observation point, an RF signal is obtained for each transmission event. Hereinafter, a plurality of RF signals pertaining to one observation point are handled as a time sequence signal sequence, and may also be referred to as an ensemble with respect to the observation point. A CFM signal is a signal indicating blood flow information for an observation point. Blood flow information is described in more detail later. FIG. 2 is a function block diagram of the CFM processor 105. As illustrated in FIG. 2, the CFM processor 105 includes a quadrature detector 1051, a filter processor 1052, a blood flow calculator 1053, a tissue velocity detector 1054, and an adaptive threshold processor 1055.

(1) Quadrature Detector 1051

Figure 3A:
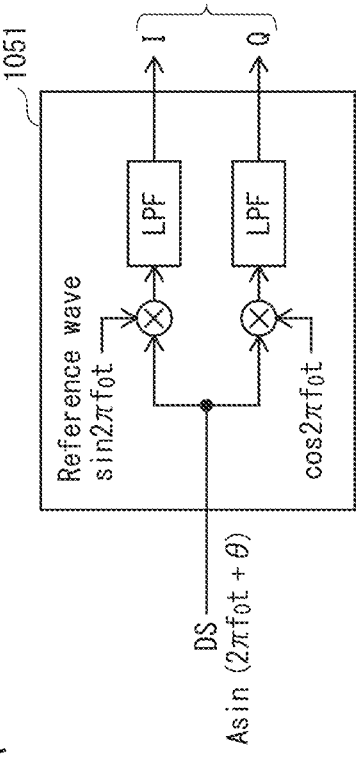
FIG. 3A is a function block diagram of a quadrature detector 1051.

The quadrature detector 1051 is a circuit that performs quadrature detection with respect to each reception signal sequence generated in correspondence with a transmission event, and generates a complex Doppler signal indicating phase of reception signals of observation points. FIG. 3A is a function block diagram of the quadrature detector 1051. Specifically the following processing is performed with respect to each acoustic line signal DS included in the ensemble of each observation point. First, a first reference signal $\sin 2\pi f_0 t$ is generated having a same frequency $f_0$ as a transmission ultrasound and a second reference signal $\cos 2\pi f_0 t$ is generated having a same frequency and amplitude as the first reference signal $\sin 2\pi f_0 t$ but a difference in phase of 90°. Next, the acoustic line signal DS, $A \sin(2\pi f_0 t+\theta)$, and the first reference signal $\sin 2\pi f_0 t$ are integrated, and a high frequency component having a frequency $4\pi f_0 t$ about twice the first reference signal $\sin 2\pi f_0 t$ is removed by LPF, obtaining a first component. Similarly, the acoustic line signal DS, $A \sin(2\pi f_0 t+\theta)$, and the second reference signal $\cos 2\pi f_0 t$ are integrated, and a high frequency component having a frequency $4\pi f_0 t$ about twice the second reference signal $\cos 2\pi f_0 t$ is removed by LPF, obtaining a second component. Next, with the first component as a real part (I component; in phase) and the second component as an imaginary part (Q component; quadrature phase), a complex Doppler signal Z1 ($Z1=I+iQ=Ae^{j\theta}$) is generated.

(2) Filter Processor 1052

Figure 3B:
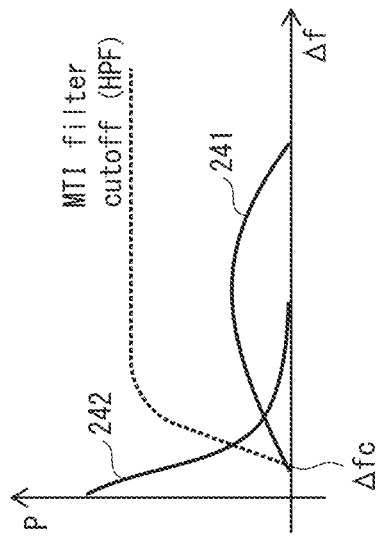
FIG. 3B is a function explanation diagram pertaining to a filter processor 1052.

The filter processor 1052 is a filter circuit that removes the clutter component 242 from the complex Doppler signal Z1. The clutter component 242 is information indicating, among tissue movement, a component that is not a visualization target such as blood vessel, muscle, and organ tissue movement. FIG. 3B is a function explanation diagram pertaining to the filter processor 1052. The filter processor 1052 is an MTI filter including a clutter removal filter such as an FIR filter. For example, as illustrated in FIG. 3B, by removing a signal having a frequency lower than a defined cutoff frequency $\Delta fc$, the clutter component 242 is reduced from the complex Doppler signal Z1 and the blood flow component 241 passes, leading to output of a complex Doppler signal Z2 (second complex Doppler signal sequence). In this way, the blood flow component 241 passes the filter processor 1052 while the clutter component 242 is removed by the filter processor 1052. The filter processor 1052 is not limited to high-pass filters such as an FIR filter and may be any filter that can remove clutter. For example, a least squares filter, a polynomial approximation filter, an eigenvector filter, or the like may be used.

(3) Blood Flow Calculator 1053

Figure 3C:
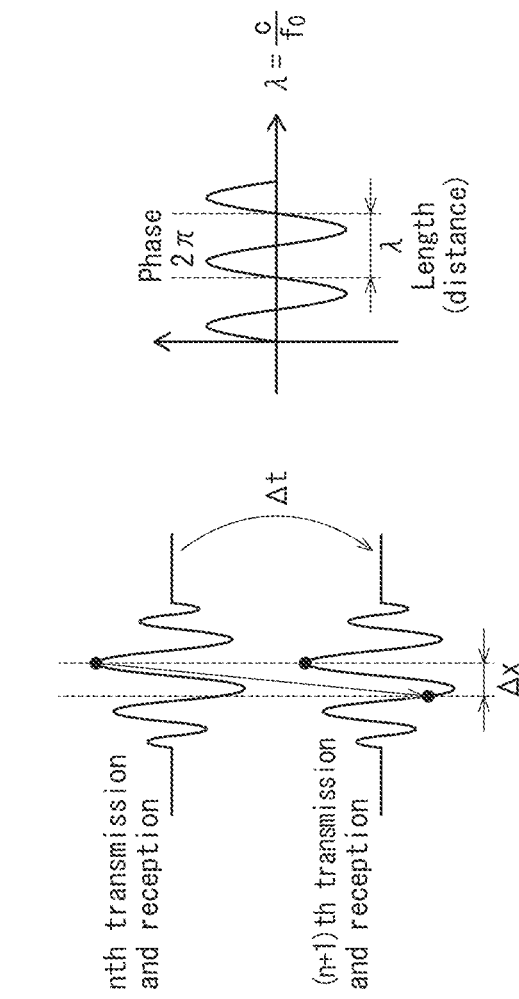
FIG. 3C is a schematic diagram for describing processing by a blood flow calculator 1053 and a tissue velocity detector 1054.

The blood flow calculator 1053 is a circuit that accepts the complex Doppler signal 72 after filter processing as input, and calculates blood flow information corresponding to each observation point. According to the present embodiment, the blood flow calculator 1053 calculates velocity value data V1 (first velocity value data) and power value data P1 (first power value data) as blood flow information. FIG. 3C is a schematic diagram for describing processing of the blood flow calculator 1053 and the tissue velocity detector 1054.

For each observation point in a region of interest ROI, the blood flow calculator 1053 estimates phase from each signal of an ensemble, and calculates a change rate of the phase.

As illustrated in FIG. 3C, with respect to an arrival distance difference $\Delta x$ of reflected ultrasound in transmission and reception of an ensemble number n and an ensemble number n+1, a velocity change V' is expressed by Equation (1), where c is light speed, $f_0$ is transmission frequency, and $\Delta\theta$ is phase change.

[Math 1]

$$V = \frac{\Delta x}{\Delta t} = \frac{c}{4\pi f_0} \frac{\Delta \theta}{\Delta t} \qquad \text{Equation (1)}$$

Where a real part of a complex Doppler signal $Z_n$, $Z_{n+1}$ obtained from an nth and an (n+1)th transmission and reception is $I_n$, $I_{n+1}$, and an imaginary part is $Q_n$, $Q_{n+1}$, the phase change $\Delta\theta$ is expressed by Equation (2).

[Math 2]

$$\Delta\theta = \tan^{-1} \frac{I_n Q_{n+1} - Q_n I_{n+1}}{I_n I_{n+1} + Q_n Q_{n+1}} \qquad \text{Equation (2)}$$

The blood flow calculator 1053 may estimate phase change velocity by performing correlation processing among a plurality of complex Doppler signals of an ensemble.

Autocorrelation between a conjugate complex number $Z_n^*$ of complex Doppler signal $Z_n$ and complex Doppler signal $Z_{n+1}$ is expressed by Equation (3).

[Math 3]

$$Z_n^* \cdot Z_{n+1} = (I_n I_{n+1} + Q_n Q_{n+1}) + j(I_n Q_{n+1} - Q_n I_{n+1}) \qquad \text{Equation (3)}$$

Phase change velocity (angular velocity) w is calculated by the Equation (4) using a real part Re and an imaginary part Im of the autocorrelation of $Z_n^*$ and $Z_{n+1}$.

[Math 4]

$$\omega = \frac{\Delta\theta}{\Delta t} = \frac{1}{\Delta t}\tan^{-1}\frac{\mathrm{Im}[Z_n^* \cdot Z_{n+1}]}{\mathrm{Re}[Z_n^* \cdot Z_{n+1}]} \quad \text{Equation (4)}$$

The blood flow calculator 1053 calculates a Doppler shift amount generated at each observation point from phase change velocity ω, and calculates blood flow velocity value data V1 from the Doppler shift amount.

The blood flow calculator 1053 sets the blood flow velocity value data V1 as a signal sequence continuing in an ultrasound transmission direction (subject depth direction), and outputs to the adaptive threshold processor 1055. The blood flow calculator 1053 may further calculate the blood flow power value data P1 based on a blood flow velocity distribution value T and a Doppler shift amount power spectrum. The blood flow power value data P1 is calculated by Equation (5).

[Math 5]

$$P = A = I^2 + Q^2 \quad \text{Equation (5)}$$

The blood flow calculator 1053 outputs the blood flow power value data P1 to the adaptive threshold processor 1055. The blood flow calculator 1053 may further calculate the blood flow velocity distribution value T and output to the adaptive threshold processor 1055.

(4) Tissue Velocity Calculator 1054

The tissue velocity calculator 1054 is a circuit that accepts the complex Doppler signal Z1 prior to MTI filter processing output from the quadrature detector 1051 as input, and calculates velocity value data Vt (tissue velocity value data) of a subject, corresponding to each observation point. Thus, movement of tissue of the subject relative to the probe 101 is calculated. In the tissue velocity detector 1054, a method of calculating the velocity value data Vt is the same as the method of calculating the velocity value data V1 in the blood flow calculator 1053. The complex Doppler signal Z1 includes tissue and blood flow information. However, tissue has a signal intensity about 60 dB greater than blood flow, and therefore tissue information (clutter) becomes dominant when calculating phase differences between ultrasound signals based on the complex Doppler signal Z1. Thus, the tissue velocity detector 1054 calculates the velocity value from the complex Doppler signal Z1 prior to MTI filter processing, and thereby obtains information equivalent to the tissue velocity value data Vt. In order to achieve greater accuracy, the tissue velocity detector 1054 may calculate the tissue velocity value data Vt after extracting tissue information by using a low pass filter or the like on the complex Doppler signal Z1.

Further, the tissue velocity detector 1054 may receive as input the complex Doppler signal Z1 prior to filter processing output from the quadrature detector 1051, and may calculate the tissue power value data Pt of a subject corresponding to each observation point according to Equation (5). In this case, the tissue velocity value data Vt can be calculated taking into consideration calculated tissue power value data Pt.

(5) Adaptive Threshold Processor 1055

The adaptive threshold processor 1055 is a circuit that receives as inputs the blood flow velocity value data V1, the blood flow power value data P1, and the tissue velocity value data Vt, and, for coordinates of each observation point, calculates blood flow velocity value data V2 (second velocity value data) based on the blood flow velocity value data V1 and the tissue velocity value data Vt, and corrects an absolute value of velocity value of the blood flow velocity value data V2 to be equal to or less than a velocity threshold Vth to calculate blood flow velocity value data V3 (third velocity value data). Further, the adaptive threshold processor 1055 may be configured to remove data of the blood flow power value data P1 with a power value equal to or less than a power value threshold Pth to calculate blood flow power value data P2 (second power value data).

Figure 4:
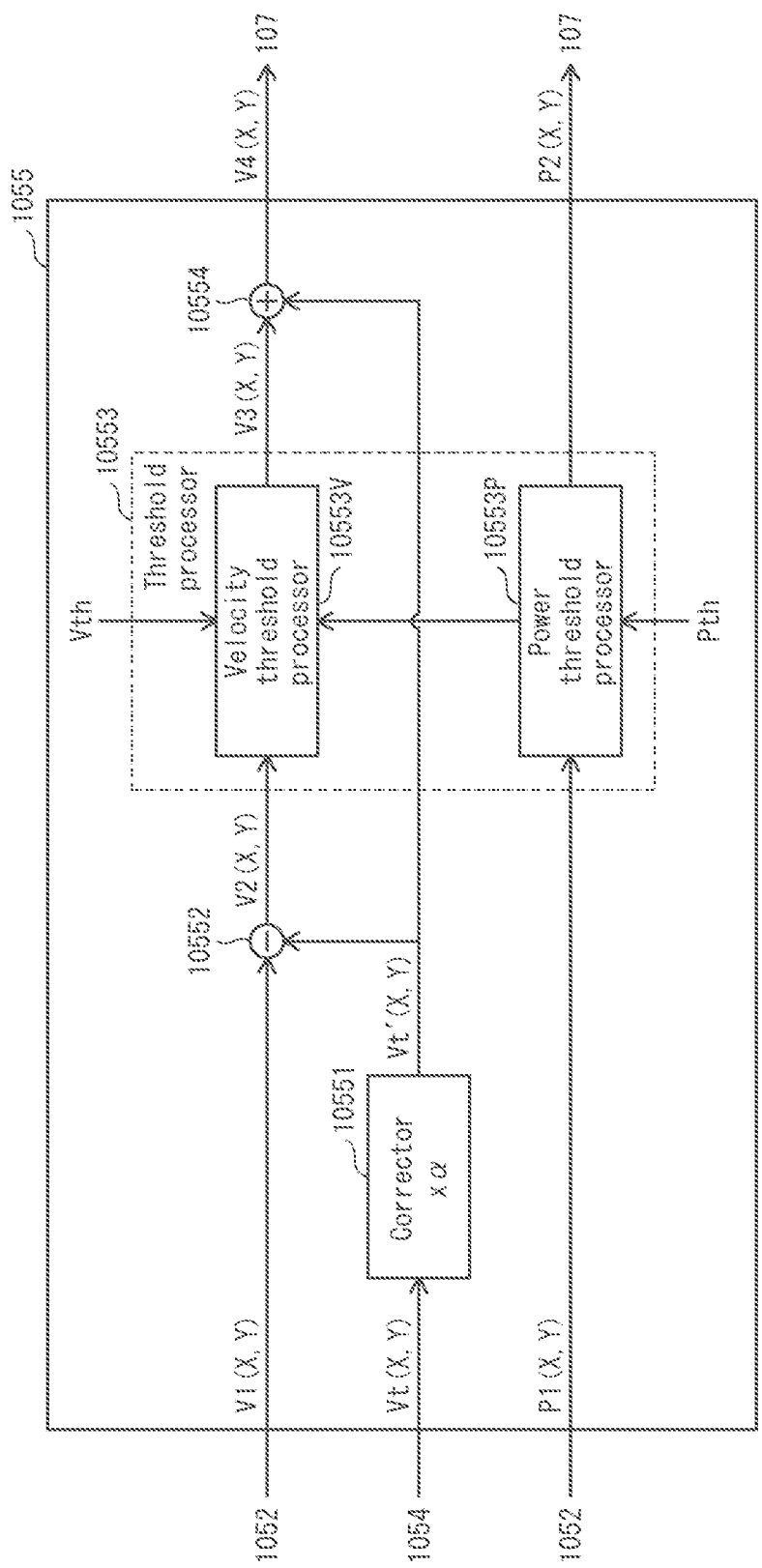
FIG. 4 is a function block diagram of an adaptive threshold processor 1055.

FIG. 4 is a function block diagram of the adaptive threshold processor 1055. As illustrated in FIG. 4, the adaptive threshold processor 1055 includes a corrector 10551, a subtractor 10552, a threshold processor 10553, and a summer 10554. Blood flow velocity value data, tissue velocity value data, and blood flow power value data are data sets per set of coordinates (X,Y) of observations points in the region of interest ROI, and therefore (X,Y) is added to the reference signs for data in the following description.

The corrector 10551 accepts as input tissue velocity value data Vt(X,Y) output from the filter processor 1052 tissue velocity detector 1054 and calculates a value based on the tissue velocity value data Vt(X,Y). For example, the corrector 10551 may be configured to correct the tissue velocity value data Vt(X,Y). In this case, correction by the corrector 10551 may be configured to multiply the tissue velocity data Vt(X,Y) by a correction coefficient α (0<α<1). Correction methods are not limited to multiplication, and other correction methods may be applied.

Figure 5:
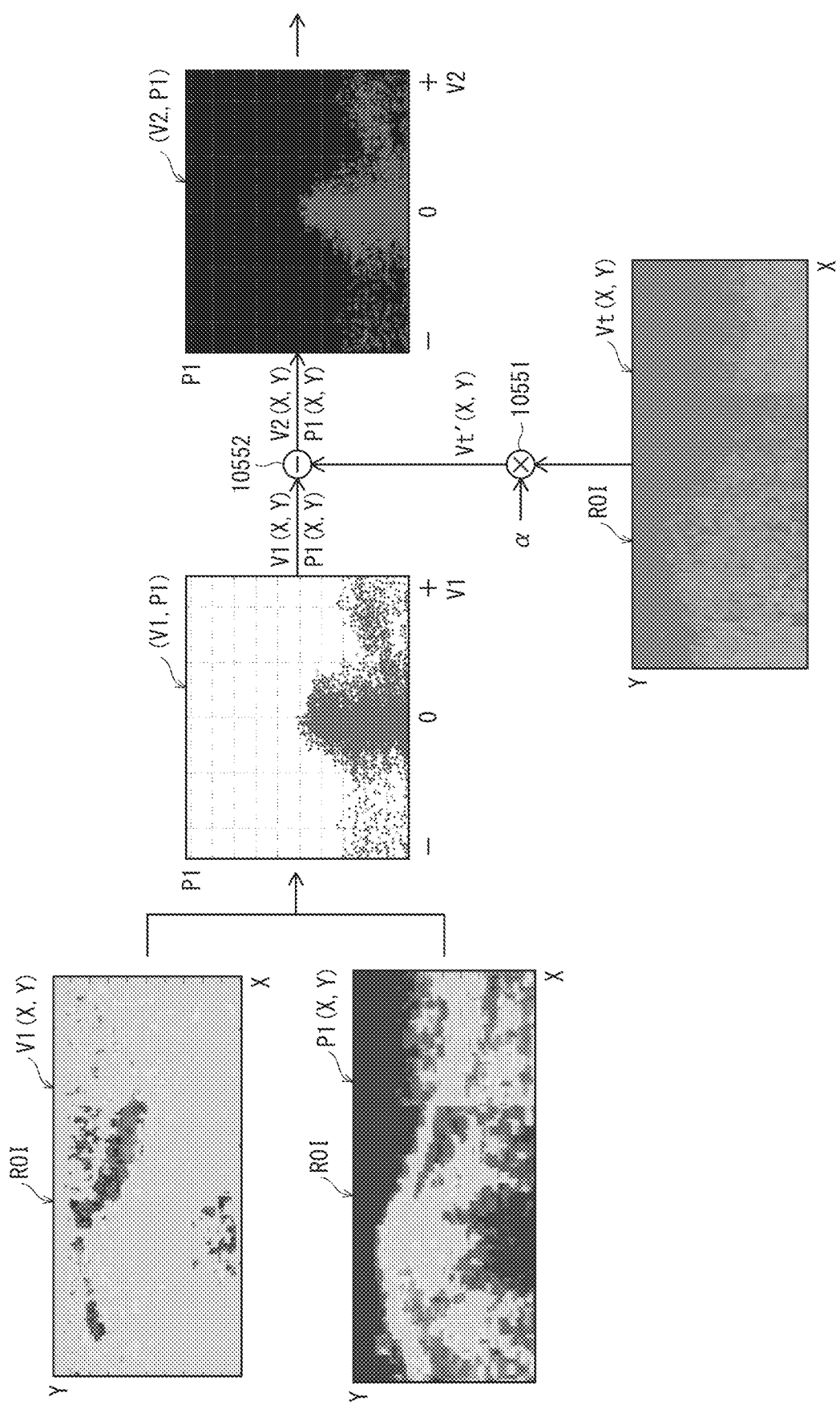
FIG. 5 is an operation explanation diagram pertaining to a subtractor 10552 in the adaptive threshold processor 1055.

The subtractor 10552 subtracts from the blood flow velocity value data V1(X,Y) a value V't(X,Y) obtained by multiplying the tissue velocity value data Vt(X,Y) by the correction coefficient α, in order to calculate blood flow velocity value data V2(X,Y). FIG. 5 is an operation explanation diagram pertaining to the subtractor 10552. As described above, the blood flow velocity value data V1(X,Y) is a data set of blood flow velocity value data V1 per set of coordinates (X,Y) of observation points in the region of interest ROI, the blood flow power value data P1(X,Y) is a data set of blood flow power value data P1 per set of coordinates (X,Y) of observation points in the region of interest ROI, and the tissue velocity value data Vt(X,Y) is a data set of tissue velocity value data Vt per set of coordinates (X,Y) of observation points in the region of interest ROI. In FIG. 5 to FIG. 7, FIG. 11, FIG. 12A, and FIG. 12B, for convenience, blood flow velocity value data V1(X,Y) and blood flow power value data P1(X,Y) are correlated with coordinates (X,Y) of observation points, and mapped (V1, P1) such that a horizontal axis is velocity value and a vertical axis is a power value. The same applies to the blood flow velocity value data V2.

The subtractor 10552 subtracts from the blood flow velocity value data V1(X,Y) the correction value V't(X,Y) obtained by multiplying the tissue velocity value data Vt(X, Y) by the correction coefficient α, in order to calculate the blood flow velocity value data V2(X,Y). As illustrated in FIG. 5, when comparing distribution states of data in which a horizontal axis represents velocity value and a vertical axis represents power value, data of a map (V2,P1) after subtraction processing is distributed more in the vicinity of an origin in the horizontal direction (velocity 0) than data of the map (V1,P1) prior to subtraction. This is because, with the subtraction of the correction value V't(X,Y) from the blood flow velocity value data Vt(X,Y), the map (V2,P1) of the blood flow velocity value data V2(X,Y) is closer to the origin in the horizontal direction than the map (V1,P1) of the blood flow velocity value data V1(X,Y) by an amount corresponding to the correction value V't(X,Y).

Figure 6:
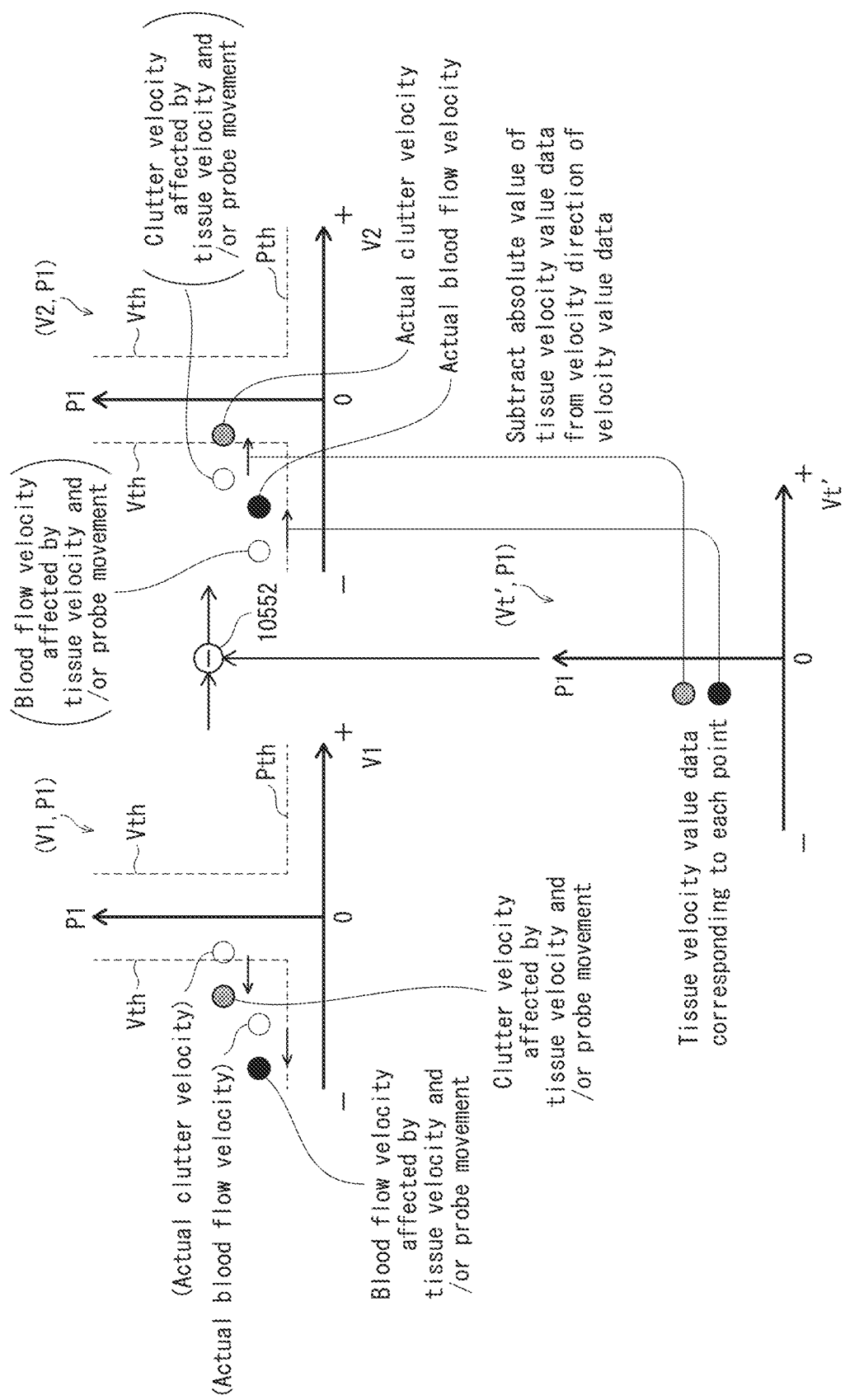
FIG. 6 is an operation explanation diagram pertaining to the subtractor 10552 in the adaptive threshold processor 1055.

FIG. 6 is an operation explanation diagram pertaining to the subtractor 10552 in the adaptive threshold processor 1055. In FIG. 6, in an upper left portion of the drawing, a leftmost empty circle "○" represents actual blood flow velocity and a rightmost empty circle "○" represents actual clutter velocity. Further, a filled circle "•" represents blood flow velocity influenced by tissue movement and/or probe movement, and a crosshatched circle represents clutter velocity influenced by tissue movement and/or probe movement.

As illustrated in FIG. 6, in the blood flow velocity value data V1(X,Y), a clutter component not removed by the filter processor 1052 is superimposed on actual blood flow velocity. The subtractor 10552 specifies coordinates where clutter exists and relative size of clutter coordinates from the tissue velocity value data Vt(X,Y) detected by the tissue velocity detector 1054. Further, through multiplication by the correction coefficient α, the value V't(X,Y) is made closer in absolute value to clutter size, then subtracted from the blood flow velocity value data V1(X,Y). Thus, the blood flow velocity value data V2(X,Y) can be accurately calculated as velocity of a moving body in a living organism with influence of tissue movement and movement of the probe 101 removed. In other words, as illustrated in the top right of FIG. 6, blood flow velocity influenced by tissue movement and/or probe movement (leftmost empty circle "○") and clutter velocity influenced by tissue movement and/or probe movement (rightmost empty circle "○") are calculated as actual blood flow velocity (filled circle "•") and actual clutter velocity (crosshatched circle), respectively.

The threshold processor 10553 includes a velocity threshold processor 10553V and a power threshold processor 10553P. The velocity threshold processor 10553V removes from the blood flow velocity value data V2(X,Y) data that has an absolute value of velocity equal to or less than the velocity threshold Vth to calculate blood flow velocity value data V3(X,Y). Thus, velocity of tissue can be detected based on Doppler signals and a clutter component caused by tissue movement can be adaptively removed from the Doppler signals.

The power threshold processor 10553P may remove from the blood flow power value data P1(X,Y) data that has a power value equal to or less than the power value threshold Pth, in order to calculate blood flow power value data P2(X,Y) (second power value data). Thus, for example, when a first power value data having a small intensity is detected, a clutter component due to noise can be adaptively removed, or the blood flow power value data P1(X,Y) can be outputted unchanged as the blood flow power value data P2(X,Y).

Figure 7:
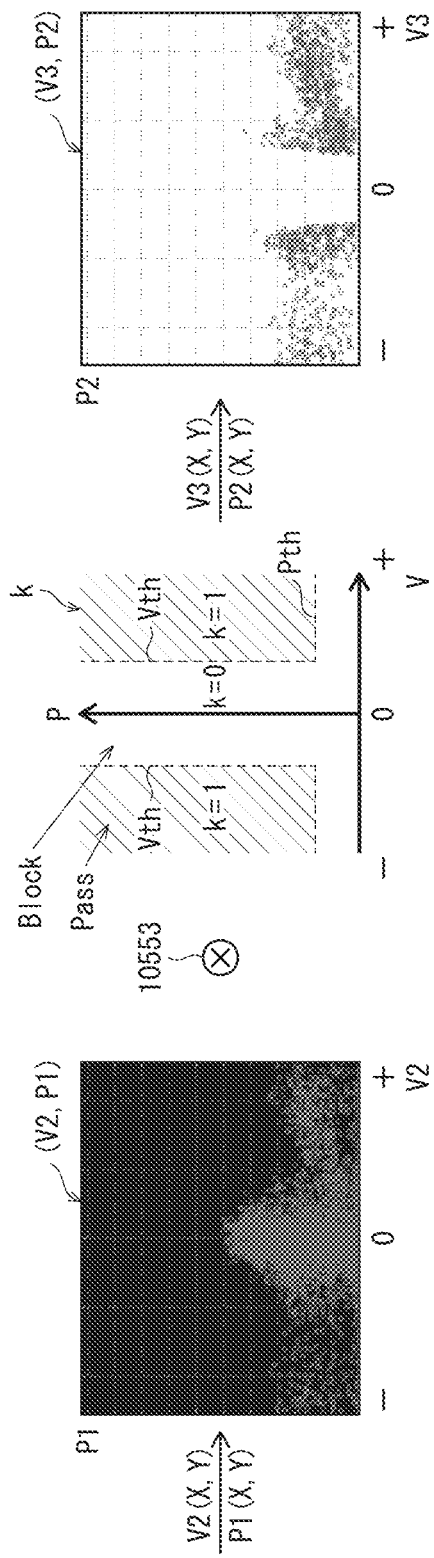
FIG. 7 is an operation explanation diagram pertaining to a threshold processor 10553 in the adaptive threshold processor 1055.

FIG. 7 is an operation explanation diagram pertaining to the threshold processor 10553 in the adaptive threshold processor 1055. In FIG. 7, for convenience, the blood flow velocity value data V2(X,Y) and the blood flow power value data P1(X,Y) are illustrated as a map (V2,P1) in which a horizontal axis is velocity value and a vertical axis is power value. The same applies to the blood flow velocity value data V3 and the blood flow power value data P2.

In threshold processing by the velocity threshold processor 10553V, with blood flow velocity value data V2(X,Y) as input, for example, multiplication by a correction coefficient k selected from a look up table (LUT) is performed such that for velocity values having an absolute value in a range equal to or less than the velocity threshold Vth the correction coefficient k has a value of 0, and outside this range the value of the correction coefficient k is 1, thereby calculating blood flow velocity value data V3(X,Y). In threshold processing by the power threshold processor 10553P, with blood flow power value data P1(X,Y) as input, for example, multiplication by correction coefficient k selected from an LUT is performed such that for power values in a range equal to or less than the power value threshold Pth the correction coefficient k has a value of 0, and outside this range the value of the correction coefficient k is 1, thereby calculating blood flow power value data P2(X,Y).

As illustrated in FIG. 7, according to threshold processing, in a map (V3,P2) of the blood flow velocity value data V3(X,Y), a certain range centered on the origin in the horizontal direction of distribution of the map (V2,P1) of the blood flow velocity value data V2(X,Y) is removed. As described above, the subtractor 10552 subtracts from the blood flow velocity value data V1(X,Y) the value V't(X,Y) obtained by multiplying the tissue velocity value data Vt(X,Y) by the correction coefficient α, thereby removing a superimposed clutter component that is not removed by the filter processor 1052 and performing processing that brings the blood flow velocity value data V2(X,Y) closer to actual blood flow velocity. Thus, the threshold processor 10553 can remove a clutter component adapted to size and distribution of actual blood flow velocity according to tissue velocity and power values.

The adaptive threshold processor 1055 may be configured to directly subtract the tissue velocity value data Vt from the blood flow power value data P1 to calculate the blood flow velocity value data V2.

Further, the adaptive threshold processor 1055 may be configured to convert to 0 any power value data in the blood flow power value data P1 that is equal to or less than the power value threshold Pth and any velocity value data in the blood flow velocity value data V2 corresponding to the same observation point coordinates, in order to calculate the blood flow velocity value data V3.

The summer 10554 sums the blood flow velocity value data V3(X,Y) and the tissue velocity value data Vt(X,Y) for each set of observation point coordinates in order to calculate blood flow velocity value data V4(X,Y) (fourth velocity value data). As a result, after removing the clutter component by adaptive threshold processing from the blood flow velocity value data V1(X,Y) from which the tissue velocity value data Vt(X,Y) is subtracted by the subtractor 10552, the result is summed with the tissue velocity value data Vt(X,Y), returning the signal to its original state based on tissue velocity.

4. Tomographic Image Processor 106

The tomographic image processor 106 performs envelope detection and logarithmic compression with respect to acoustic line signals pertaining to one transmission event generated by the reception beamformer 104, in order to generate one frame of B mode image data. Generated B mode image data is outputted to the image generator 107 and the data storage 109.

5. Image Generator 107

The image generator 107 is a circuit that performs color tone conversion on CFM signals (velocity value data V4(X,Y)) generated by the CFM processor 105 and superimposes the result on a B mode tomographic image generated by the tomographic processor 106 to generate a color Doppler image. Further, the image generator 107 may perform color tone conversion on CFM signals (power value data P2(X,Y)) generated by the CFM processor 105 and superimpose the result on a B mode tomographic image generated by the tomographic processor 106 to generate a power Doppler image.

In the case of generating a color Doppler image, the following processing is performed. The image generator 107 first converts a coordinate system of CFM signals (velocity value data V4(X,Y)) to an orthogonal coordinate system. Next, an average velocity V of each observation point is converted to color information to generate color flow information. At this time, conversion may be performed such that, for example, (1) a direction towards the probe is red and a direction away from the probe is blue, and (2) the greater an absolute value of velocity, the higher saturation and the smaller the absolute value of velocity, the lower the saturation. More specifically, the absolute value of a velocity component towards the probe is converted to a red luminance value, and the absolute value of a velocity component away from the probe is convened to a blue luminance value. The image generator 107 may further receive a signal T indicating velocity dispersion from the CFM processor 105, and convert the dispersion value into a green luminance value. In this way, it is possible to indicate a position in which turbulence occurs. Finally, the image generator 107 superimposes the color flow information described above on the B mode tomographic image generated by the tomographic image processor 106 to generate a color Doppler image. The color Doppler image is outputted to the display 108.

In the case of generating a color Doppler image, the following processing is performed. The image generator 107 first converts a coordinate system of CFM signals (power value data P2(X,Y)) to an orthogonal coordinate system. Next, power P for each set of observation points is convened to color information to generate power Doppler information. At this time, for example, conversion is performed such that the greater intensity of a phase difference signal, the higher the luminance and the smaller the intensity of the phase difference signal, the lower the luminance. More specifically, a point where blood flow power is equal to or above a defined value is indicated by bright yellow, a point where blood flow power is less than the defined value is indicated by dark orange, and a point where blood flow power can be regarded as zero is indicated as colorless (transparent). Finally, the image generator 107 superimposes the color information described above on the B mode tomographic image generated by the tomographic image processor 106 to generate a power Doppler image. The power Doppler image is outputted to the display 108.

<Operations>

The following describes operations of the ultrasound diagnostic device 100 configured as described above.

Figure 8:
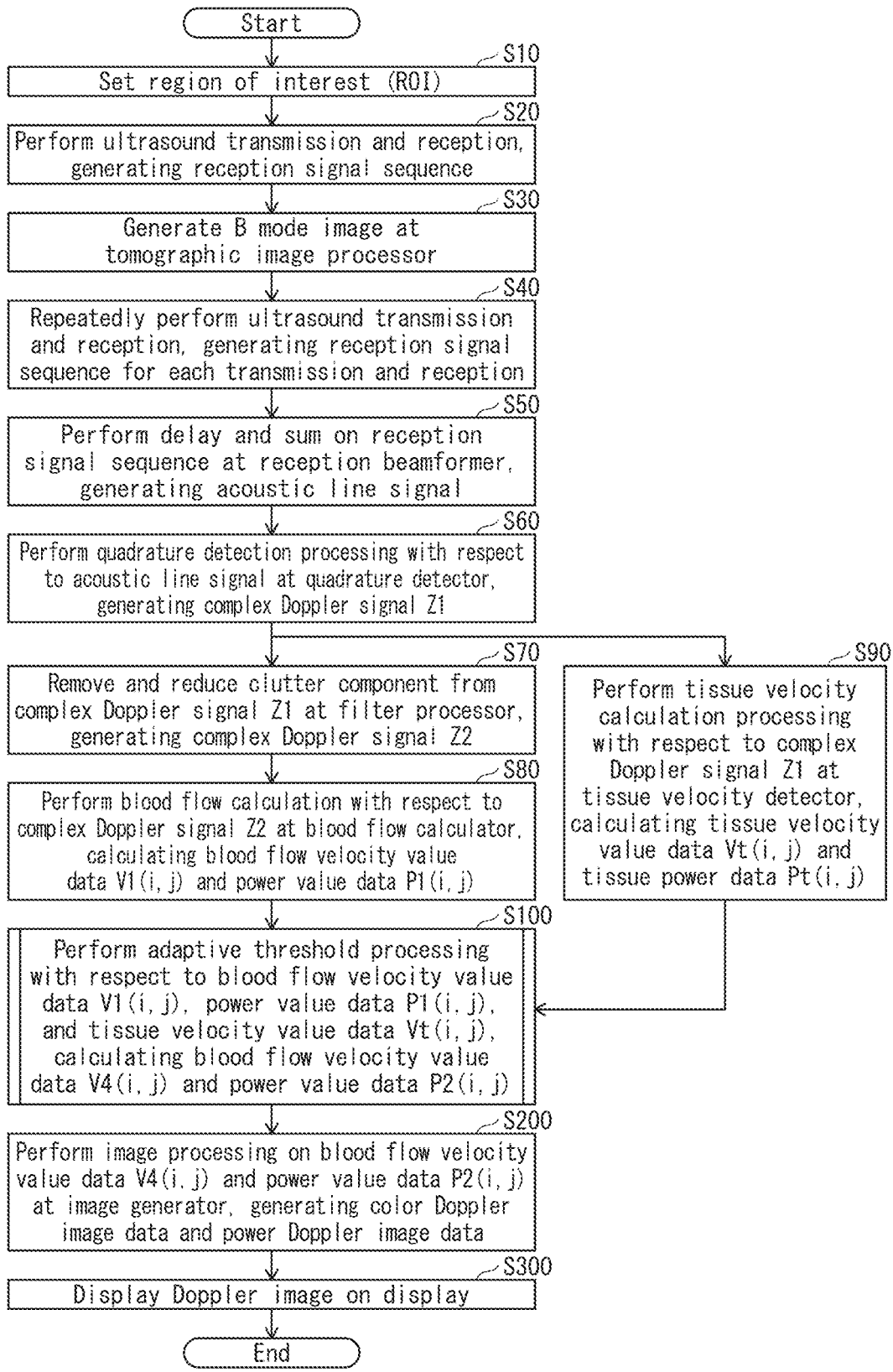
FIG. 8 is a flowchart illustrating operations of an ultrasound diagnostic device 100.

FIG. 8 is a flowchart illustrating operations of the ultrasound diagnostic device 100. In the following description of operations, coordinates X and Y of observation points are replaces by indices i and j, respectively.

First, in step S10, a region of interest (ROI) is set. As a method of setting the region of interest, for example, a B mode tomographic image acquired in advance is displayed on the display 108 and a user is instructed to designate the region of interest through an input unit (not illustrated) such as a touch panel, mouse, trackball, or the like. The method of setting the region of interest is not limited to this example. As other examples, an entire region of the B mode tomographic image may be the region of interest, or a constant range including a central portion of the B mode tomographic image may be the region of interest.

Next, the reception beamformer 104 transmits and receives ultrasound to and from a region in a subject including the region of interest, and generates a reception signal sequence based on reflected ultrasound (step S20). More specifically, an RF signal is generated based on one or more transmission events and reflected ultrasound required to generated a one-frame reception signal sequence, and a plurality of RF signals are arranged in a time sequence to generate a reception signal sequence according to reception processing.

Next, a B mode tomographic image is generated (step S30). More specifically, the reception beamformer 104 performs delay and sum processing on the reception signal sequence obtained in step S20 to generate an acoustic line signal, and the tomographic image processor 106 performs envelope detection and logarithmic compression with respect to the acoustic line signal in order to generate a B mode tomographic image. Generated B mode image data is outputted to the image generator 107 and the data storage 109.

Next, transmission and reception of ultrasound to and from the region of interest is performed multiple times, and a process of generating a reception signal sequence based on reflected ultrasound is performed for each ultrasound transmission (step S40). More specifically, at least one transmission event set is performed, an RF signal is generated based on reflected ultrasound for each transmission event included in a transmission event set, and a reception signal sequence is generated according to reception processing.

Next, a delay-and-sum process is performed with respect to the reception signal sequence obtained by the reception beamformer 104 in order to generate an acoustic line signal (step S50).

Next, the quadrature detector 1051 performs quadrature detection with respect to RF signals and generates a complex Doppler signal Z1 (step S60). As a result, an ensemble is acquired for each observation point in the region of interest.

Next, the filter processor 1052 performs MTI filter processing with respect to the complex Doppler signal Z1, and by removing a signal having a frequency lower than a defined cutoff frequency Δfc, the complex Doppler signal Z2 is generated having a reduced clutter component and a blood flow component that passes the filter processing (step S70).

Next, the blood flow calculator 1053 accepts the complex Doppler signal Z2 as input, calculates blood flow with respect to the complex Doppler signal Z2 corresponding to each observation point, and calculates the blood flow velocity value data V1 (step S80). As blood flow calculation, after making each complex Doppler signal extracted from an ensemble a combination of an I component I' and a Q component Q', for each observation point, a phase change indicated by the combination of the I component I' and the Q component Q' in the ensemble can be calculated.

More specifically, a Doppler shift amount for each observation point derived from a phase change $\Delta\theta$ and phase change rate $\omega$ between complex Doppler signals $Z_n$, $Z_{n+1}$, obtained from nth and (n+1)th transmission events is calculated via autocorrelation calculation between the conjugate complex number $Z_n^*$ of the complex Doppler signal $Z_n$ and the complex Doppler signal $Z_{n+1}$, and the blood flow velocity value data V1(i,j) is calculated from the Doppler shift amounts. Further, the power value data P1(i,j) is calculated based on the complex Doppler signal Z obtained from each transmission event.

The tissue velocity detector 1054 accepts the complex Doppler signal Z1 as input, calculates tissue velocity with respect to the complex Doppler signal Z1 corresponding to each observation point, and calculates the tissue velocity value data Vt (step S90). Calculation of the tissue velocity is by the same processing as in step S80. That is, a Doppler shift amount for each observation point derived from a phase change $\Delta\theta$ and phase change rate $\omega$ between complex Doppler signals $Z_n$, $Z_{n+1}$ obtained from nth and (n+1)th transmission events is calculated via autocorrelation calculation between the conjugate complex number $Z_n^*$ of the complex Doppler signal $Z_n$ and the complex Doppler signal $Z_{n+1}$, and the tissue velocity value data Vt(i,j) is calculated from the Doppler shift amounts. Further, the tissue power value data Pt(i,j) may be calculated based on the complex Doppler signal Z obtained from each transmission event. The tissue velocity value data Vt(i,j) can be calculated in view of calculated tissue power value data Pt(i,j). For example, there is a high possibility that a portion where the tissue power value data Pt(i,j) is equal to or less than a defined threshold is a large blood vessel such as a carotid artery, and a process of setting a value of tissue velocity value data Vt(i,j) to zero may be performed. The reason for this is that if tissue velocity is subtracted front a large blood flow such as that of a carotid artery, there is a possibility of subtraction from the blood flow occurring.

Next, the adaptive threshold processor 1055 accepts the blood flow velocity value data V1(i,j), the blood flow power value data P1(i,j), and the tissue velocity value data Vt(i,j) as input, performs adaptive threshold processing, and calculates the blood flow velocity value data V4(i,j) and the blood flow power value data P2(i,j) (step S100). More specifically, for each set of observation point coordinates, the blood flow velocity value data V2(i,j) is calculated based on the blood flow velocity value data V1(i,j) and the tissue velocity value data Vt(i,j), and velocity of the blood flow velocity value data V2(i,j) is corrected to an absolute value equal to or less than the velocity threshold Vth to calculate the blood flow velocity value data V3. Further, in the blood flow power value data P1(i,j), a power value equal to or less than the power value threshold Pth may be assumed to be noise and removed in order to calculate the blood flow power value data P2(i,j).

Figure 9:
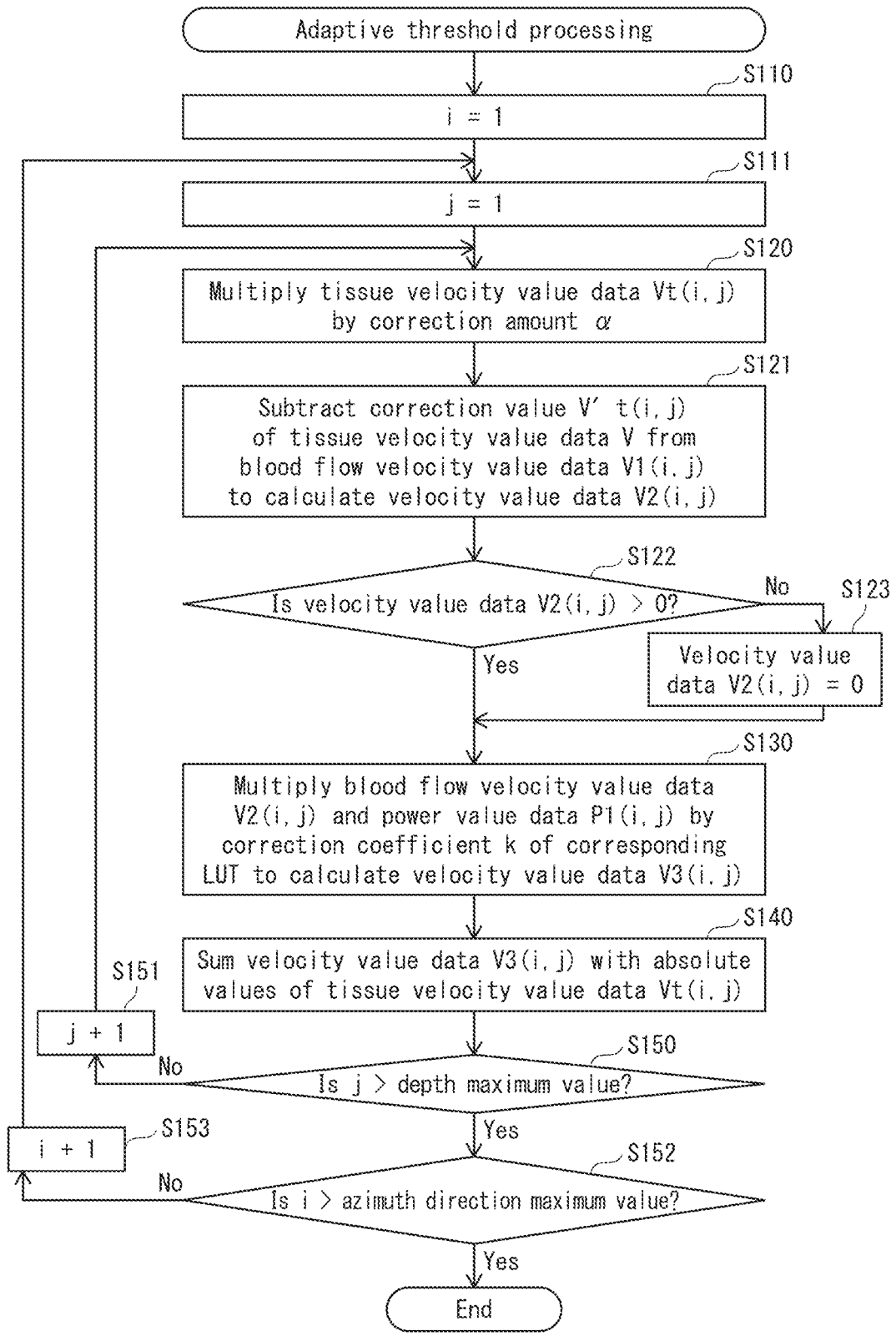
FIG. 9 is a flowchart illustrating adaptive threshold processing in step S100 of FIG. 8.

FIG. 9 is a flowchart illustrating adaptive threshold processing in step S100. After initializing the indices i and j that indicate observation point coordinates X and Y (steps S110 and S111), the corrector 10551 multiplies the tissue velocity value data Vt(i,j) outputted from the filter processor 1052 by the correction coefficient $\alpha$ (0<$\alpha$<1) (step S120).

Next, the subtractor 10552 subtracts from the blood flow velocity value data V1(i,j) the value V't(i,j) obtained by multiplying the tissue velocity value data Vt(i,j) by the correction coefficient $\alpha$, in order to calculate the blood flow velocity value data V2(i,j) (step S121). Next, whether or not the blood flow velocity value data V2(i,j) exceeds zero is determined (step S121). If not, V2(i,j)=0 and processing proceeds to step S130. If V2(i,j) exceeds zero, processing proceeds to step S130.

Next, in step S130, the threshold processor 10553 multiplies the blood flow velocity value data V2(i,j) and the power value data P1(i,j) by a correction coefficient k of a corresponding LUT. More specifically, the velocity threshold processor 10553V selects the correction coefficient k from an LUT such that in a range in which an absolute value of velocity is equal to or less than the velocity threshold Vth the correction coefficient k is 0, and outside that range the correction coefficient k is 1, then multiplies the blood flow velocity value data V2(i,j) by the correction coefficient k to calculate the blood flow velocity value data V3(i,j). The power threshold processor 10553P selects the correction coefficient k from an LUT such that in a range in which equal to or less than the power value threshold Pth the correction coefficient k is 0, and outside that range the correction coefficient k is 1, then multiplies the power value data P1(i,j) by the correction coefficient k to calculate the power value data P3(i,j).

Next, in step S140, the absolute value of the tissue velocity value data Vt(i,j) is added to the velocity value data V2(i,j) to calculate the velocity value data V4(i,j). Thus, after a clutter component is removed by adaptive threshold processing subtracting the tissue velocity value data Vt(i,j) from the blood flow velocity data V1(i,j) in step S121, the tissue velocity value data Vt(i,j) is added in step S140, returning the signal to its original state based on the tissue velocity. Next, whether or not j exceeds a depth maximum value is determined (step S150). If not, j is incremented (step S151) and processing returns to step S120. If it does, whether or not i exceeds an azimuth direction maximum value is determined (step S152). If not, i is incremented (step S153) and processing returns to step S111. If it does, processing ends.

Next, returning to FIG. 8, in step S200, the image generator 107 generates color Doppler image data by performing color tone conversion on the blood flow velocity value data V4(i,j) generated by the CFM processor 105. By performing color tone conversion on the blood flow power value data P2(i,j) generated by the CFM processor 105, power Doppler image data may be generated (step S200). For color tone conversion, with regard to average velocity included in an input signal, direction is converted into color and size is converted into luminance.

Finally, a Doppler image is displayed (step S300). More specifically, the image generator 107 superimposes the color Doppler image or power Doppler image generated in step S200 on the B mode tomographic image generated in step S30, and causes the result to be displayed by the display 108.

Effects

The following is a description of effects of clutter removal by the ultrasound signal processing device 150.

1. Embodiment and Reference Example

The inventor performed an evaluation of effects of clutter removal by the ultrasound signal processing device 150. An embodiment is specified using the configuration of the CFM processor 105 illustrated in FIG. 2 in the ultrasound signal processing device 150 illustrated in FIG. 1.

Figure 10A:
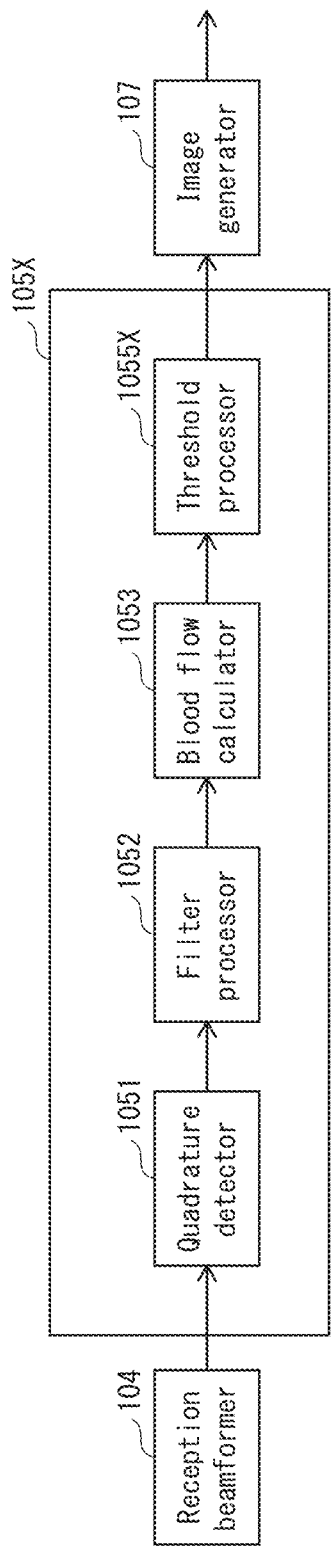
FIG. 10A is a function block diagram of a CFM processor 105X pertaining to a reference example.
Figure 10B:
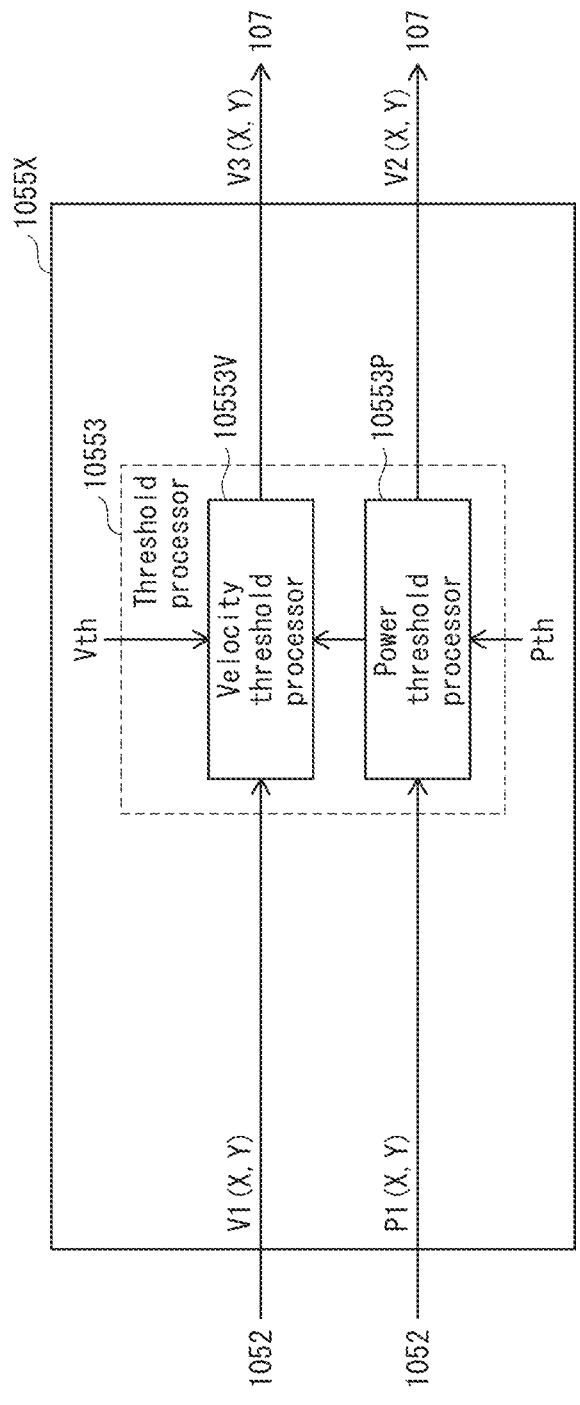
FIG. 10B is a function block diagram of a threshold processor 1055X.
Figure 11:
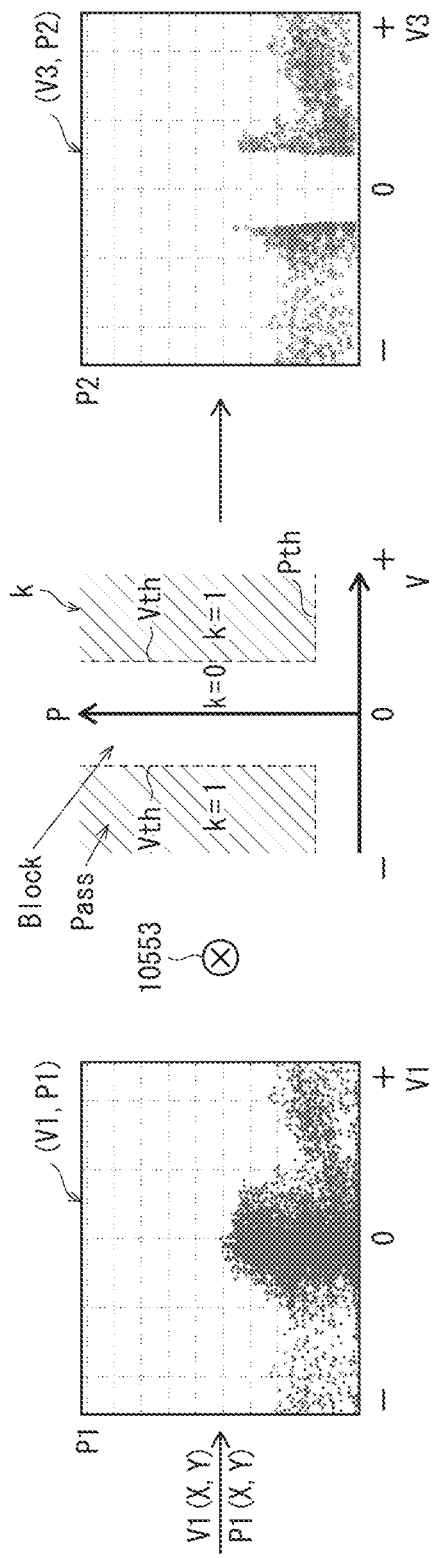
FIG. 11 is an operation explanation diagram pertaining to the threshold processor 1055X of the reference example.

FIG. 10A is a function block diagram of a CFM processor 105X pertaining to a reference example. The reference example is specified using the configuration of the CFM processor 105X illustrated in FIG. 10A in the ultrasound signal processing device 150 illustrated in FIG. 1. The CFM processor 105X has a configuration such that the tissue velocity detector 1054 is removed from the CFM processor 105 and the adaptive threshold processor 1055 is replaced with a threshold processor 1055X. FIG. 10B is a function block diagram of the threshold processor 1055X. The threshold processor 1055X is equivalent to the adaptive threshold processor 1055 from which everything aside from the threshold processor 10553 is removed. In the threshold processor 1055X, the velocity threshold processor 10553V accepts as input the velocity value data V1(X,Y) outputted from the filter processor 1052, and calculates the velocity value data V3(X,Y) by removing from the velocity value data V1(X,Y) absolute velocity values equal to or less than the velocity threshold Vth. The power threshold processor 10553P removes from the blood flow power value data P1(X,Y) data that has a power value equal to or less than the power threshold Pth, in order to calculate the blood flow power value data P2(X,Y). FIG. 11 is an operation explanation diagram pertaining to the threshold processor 1055X. Threshold processing in the velocity threshold processor 10553V is the same as the processing illustrated in FIG. 7, except that the input signal is the velocity value data V1(X,Y) output from the filter processor 1052. Further, threshold processing in the power threshold processor 10553P is the same as the processing illustrated in FIG. 7.

2. Evaluation Results

First, distribution of velocity value data and power value data obtained by the embodiment and the reference example are compared.

Figure 12A:
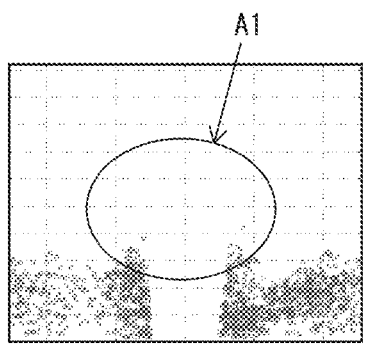
FIG. 12A is a velocity/power distribution diagram illustrating distribution of velocity data and power data for each set of observation point coordinates in a region of interest according to processing by the adaptive threshold processor 1055.
Figure 12B:
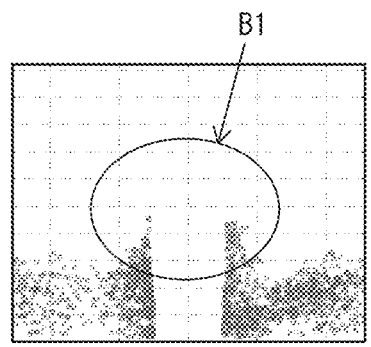
FIG. 12B is a velocity/power distribution diagram illustrating distribution of velocity data and power data for each set of observation point coordinates in a region of interest according to processing by the threshold processor 1055X of the reference example.

FIG. 12A is a velocity/power distribution diagram illustrating distribution of velocity data and power data for each set of observation point coordinates in a region of interest according to processing by the adaptive threshold processor 1055 of the embodiment, and FIG. 12B is a velocity/power distribution diagram illustrating distribution of velocity data and power data for each set of observation point coordinates in a region of interest according to processing by the threshold processor 1055X of the reference example. According to FIG. 12A and FIG. 12B, data is removed in a certain range around the origin of the horizontal axis due to threshold processing. It can be seen that in the area indicated as A1 in FIG. 12A pertaining to the embodiment, distribution density of data on both left and right sides of the data removal range is less than in the area indicated as B1 in FIG. 12B pertaining to the reference example. Considering this result, according to the embodiment, along with subtraction of the correction amount V't(X,Y) of the velocity value data Vt(X,Y), in the input stage of threshold processing, in the velocity/power distribution diagram pertaining to the embodiment, distribution of data is shifted towards the origin of the horizontal axis by an amount corresponding to the correction value V't(X,Y), and therefore more data is removed in the data removal range than in the velocity/power distribution diagram pertaining to the reference example. From this state, furthermore, in the embodiment, by performing threshold processing, more data in the data removal range is removed.

Figure 13A:
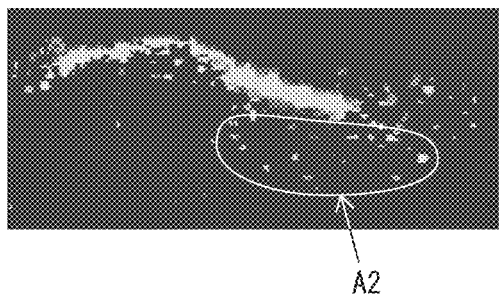
FIG. 13A is a color Doppler image including a finger joint cross-section in a region of interest according to processing by the adaptive threshold processor 1055.
Figure 13B:
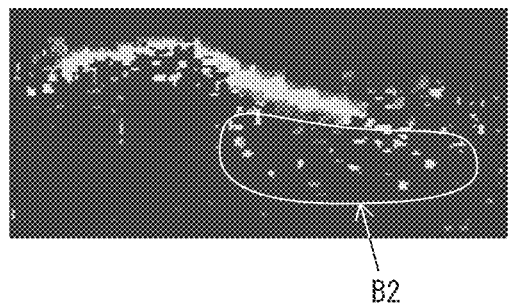
FIG. 13B is a color Doppler image including a finger joint cross-section in a region of interest according to processing by the threshold processor 1055X of the reference example.
Figure 14A:
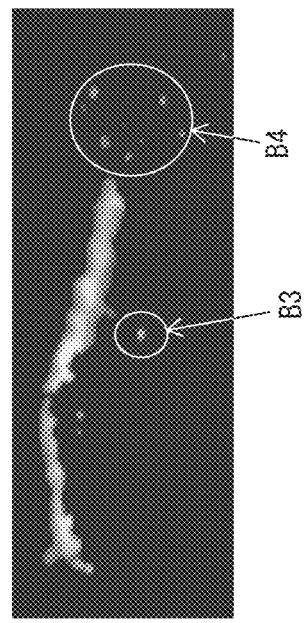
FIG. 14A is a power Doppler image of a finger joint cross-section according to processing by the adaptive threshold processor 1055.
Figure 14B:
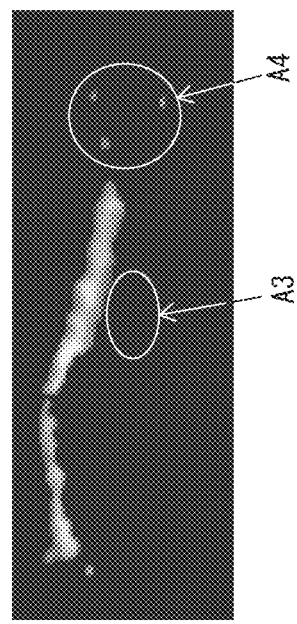
FIG. 14B is a power Doppler image of a finger joint cross-section according to processing by the threshold processor 1055X of the reference example.

The following is a comparison of display images according to the embodiment and the reference example. FIG. 13A and FIG. 13B are color Doppler images of a finger joint side cross section and FIG. 14A and FIG. 14B are power Doppler images of the finger joint side cross section. FIG. 13A and FIG. 14A illustrate a case of processing according to the adaptive threshold processor 1055 pertaining to the embodiment and FIG. 13B and FIG. 14B illustrate a case of processing according to the threshold processor 1055X pertaining to the reference example. It can be seen that bright spots due to clutter in regions indicated as B2, B3, and B4 in FIG. 13B and FIG. 14B pertaining to the reference example are reduced in regions indicated as A2, A3, and A4 in FIG. 13A and FIG. 14A pertaining to the embodiment.

<Partial Summary>

As described above, the ultrasound signal processing device pertaining to the present embodiment includes the following features: a quadrature detector that generates, for each detection wave, a first complex Doppler signal sequence through quadrature detection of a reception sequence; a tissue velocity detector that generates tissue velocity value data by calculating velocity values for each set of coordinates of observation points in a region of interest from the first complex Doppler signal sequence; a filter processor that generates a second complex Doppler signal sequence by performing clutter removal filter processing on the first complex Doppler signal sequence; a blood flow calculator that generates first velocity value data by calculating velocity values for each set of coordinates of the observation points from the second complex Doppler signal sequence; and an adaptable threshold processor that generates, for each set of coordinates of the observation points, (i) second velocity value data based on the first velocity value data and the tissue velocity value data, and (ii) third velocity value data by applying a correction to velocity values of the second velocity value data that have an absolute value equal to or less than a velocity threshold.

According to this configuration, velocity of tissue can be detected based on Doppler signals and a clutter component caused by tissue movement can be adaptively removed from the Doppler signals. This makes it possible to extract the blood flow component with high accuracy while reliably removing the clutter component. Thus, the blood flow component can be extracted with high accuracy and Doppler image quality can be improved.

According to a conventional method of applying motion correction detected from a B mode tomographic image to a corresponding Doppler image, a correction value for the Doppler image is calculated from the B mode tomographic image based on echo signals pertaining to a different transmission and reception, and therefore when the movement velocity of tissue with respect to a probe is high, there is a problem that excess or deficiency occurs in the magnitude of the clutter component to be removed, and the clutter cannot be sufficiently removed.

However, according to the ultrasound signal processing method pertaining to the present embodiment, a clutter component is detected from a signal from the same transmission and reception sequence as the Doppler signal to be corrected, and where the clutter signal exists in the same range as the Doppler signal, adaptive correction is performed according to size of the clutter component, and therefore Doppler image quality is improved when compared with a conventional clutter removal method in which transmission and reception sequences are different for acquisition of a signal used to determine a correction value and acquisition of a signal to be corrected.

Modifications

According to Embodiment 1, in the processing of step S100 by the adaptive threshold processor 1055, in step S130, the threshold processor 10553 calculates the velocity value data V3(i,j) by multiplying the blood flow velocity value data V2(i,j) and the power value data P2(i,j) by the correction coefficient k from corresponding LUTs. and then, in step S140, the absolute value of the tissue velocity value data Vt(i,j) is added to the velocity value data V3(i,j). Further, the correction coefficient k is selected from an LUT such that, for a range of absolute velocity values equal to or less than the velocity threshold Vth the correction coefficient k is 0 and outside this range the correction coefficient k is 1, and the velocity value data V3(i,j) is calculated by multiplying the velocity value data V2(i,j) by the correction coefficient k. However, it is also possible to adopt the following method of adaptively changing the correction coefficient k of the LUT according to the tissue velocity value data Vt(i,j).

Operations

Figure 15:
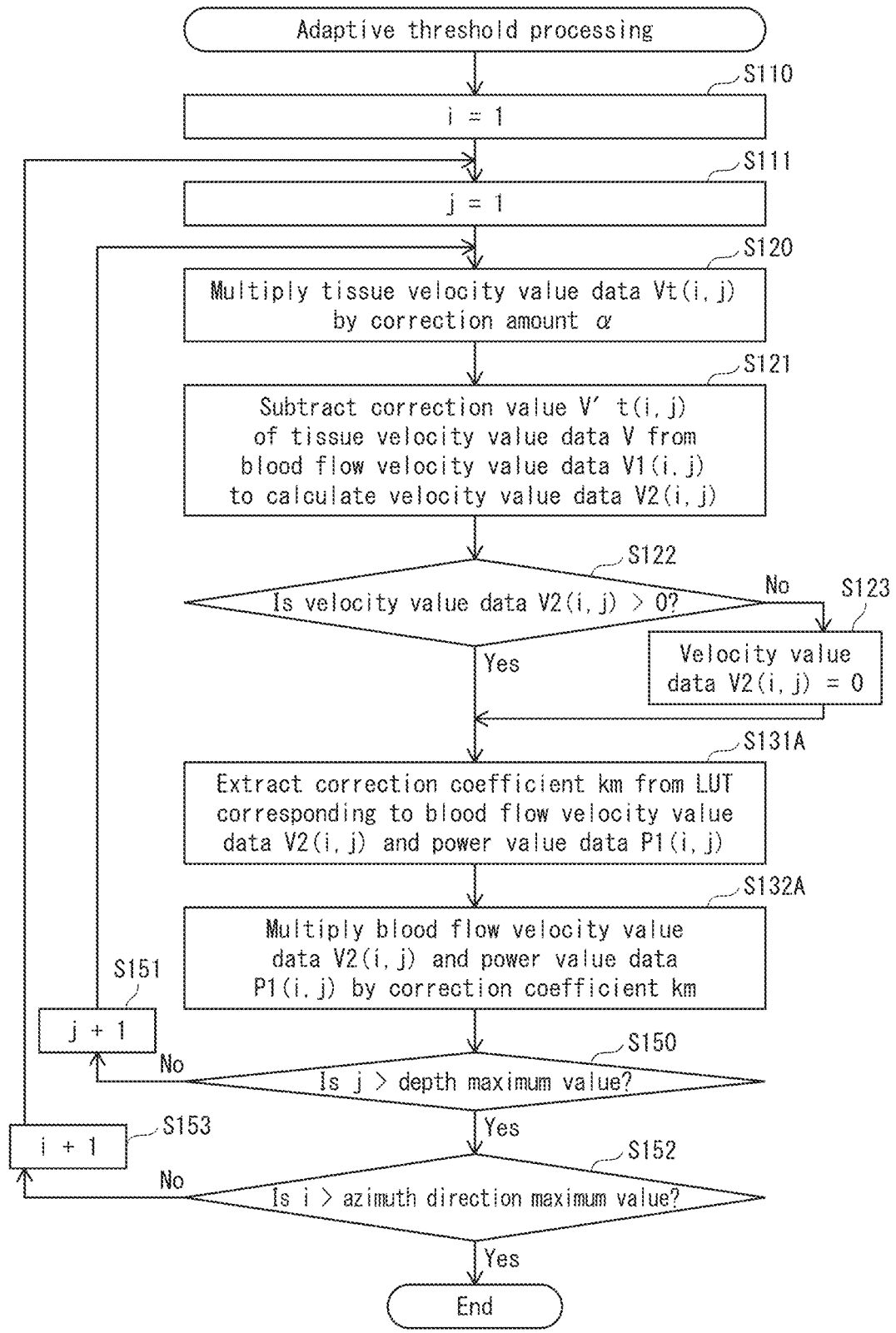
FIG. 15 is a flowchart illustrating processing by the adaptive threshold processor 1055 pertaining to a modification.

The following is a description of processing by the adaptive threshold processor 1055 pertaining to a modification, with reference to FIG. 15. FIG. 15 is a flowchart illustrating processing by the adaptive threshold processor 1055 pertaining to a modification. Operations that are the same as in FIG. 9 are assigned the same step numbers, and description thereof is not repeated here.

In step S131A, the threshold processor 10553 extracts a correction coefficient km of an LUT corresponding to the blood flow velocity value data V2(i,j) and the blood flow power value data P1(i,j). The correction coefficient km, in a range 0<km<1, for example, is adaptively determined according to the blood flow velocity value data V2(i,j) and the power value data P1(i,j) for each set of observational coordinates i,j. As a result, the correction coefficient km can be set for each set of observational coordinates i, j, reflecting distribution of the tissue velocity value data Vt(i,j) and the tissue power value data Pt(i,j).

Next, in step S132A, the threshold processor 10553 multiplies the blood flow velocity value data V2(i,j) and the power value data P1(i,j) by the correction coefficient km for each set of observational coordinates i,j, in order to generate the blood flow velocity value data V3(i,j) and the power value data P2(i,j).

Next, in FIG. 8, in step S200, the image generator 107 generates color Doppler image data by performing color tone conversion on the blood flow velocity value data V3(i,j) generated by the CFM processor 105. By performing color tone conversion on the blood flow power value data P2(i,j) generated by the CFM processor 105, power Doppler image data may be generated (step S200).

<Partial Summary>

As described above, in an ultrasound signal processing device that uses the adaptive threshold processor 1055A pertaining to a modification, a configuration is adopted that generates velocity value data V3(X,Y) by calculating a coefficient km applicable to data in which velocity values of blood flow velocity value data V2(X,Y) have an absolute value equal or less than a velocity threshold Vth, and multiplying the velocity value data V2(X,Y) by the coefficient km. Further, the ultrasound signal processing device may be configured to generate power value data P2(X,Y) by calculating a coefficient km applicable to data in which power values of blood flow power value data P1(X,Y) have an absolute value equal to or less than a power value threshold Pth. and multiplying the power value data P1(X,Y) by the coefficient kin.

Further, the ultrasound signal processing device may be configured such that the blood flow calculator further generates first power value data P1(X,Y) by calculating a power value for each set of coordinates of the observation points from the second complex Doppler signal sequence; the adaptive threshold processor 1055A generates second power value data P2(X,Y) by calculating a coefficient km applicable to data in which the velocity values of the second velocity value data V2(X,Y) have an absolute value equal to or less than a velocity value threshold Vth, and multiplying the first power value data P1(X,Y) by the coefficient km; and the image generator 107 further generates power Doppler image data based on the second power value data P2(X,Y).

According to this configuration, it is possible to eliminate processing summing the velocity value data V3(i,j) with absolute values of the tissue velocity value data Vt(i,j). Thus, in addition to the effects according to Embodiment 1, it is possible to reduce computation and processing load, leading to an increase in processing speed.

According to the ultrasound signal processing device, the ultrasound signal processing method, and the ultrasound diagnostic device that makes use of same, each pertaining to an aspect of the present invention, velocity of tissue is detected based on a Doppler signal and a clutter component caused by movement of the tissue in the Doppler signal can be adaptively removed according to the velocity of the tissue. Thus, a blood flow component can be extracted with high accuracy, and Doppler image quality can be improved.

Other Modifications (1) According to the embodiments and modifications, an MTI filter is implemented with respect to complex Doppler signals or complex acoustic line signals obtained by quadrature detection as complex numbers for which an I component is a real part and a Q component is an imaginary part. However, for example, an MTI filter may be implemented for an I component and a Q component independently of each other. In such a case, for example, instead of the filter processor 1052, the CMF processor includes two filter processors that do not include a complexing unit or an imaginary/real separation unit, and MTI filtering can be implemented such that with respect to the I component, one filter processor creates a filter based on the real number component and applies the filter to the real number component and with respect to the Q component, the other filter processor creates a filter based on the real number component and applies the filter to the real number component. In this case, the two filter processors may use the same region as a filter source region.

(2) According to the embodiments and modifications, the CFM processor 105 generates a CFM signal based on the reception signal. However, for example, the CFM processor may generate a CFM signal based on an acoustic line signal after delay-and-sum processing. In this case, the reception beamformer generates an acoustic line signal by performing delay-and-sum for each transmission event when generating an ensemble, and the CFM processor performs quadrature detection on the acoustic line signal to generate a complex acoustic line signal, and performs velocity analysis after performing MTI filter processing on the complex acoustic line signal.

According to Embodiment 1, an RF signal used for generating a B mode image is acquired separately from an RF signal used for generating a CFM signal, but an RF signal used for generating a B mode image may be used as a first ensemble. Further, when a CFM signal is generated based on an acoustic line signal after delay-and-sum, an acoustic line signal for generating a B mode signal may be used as the first ensemble.

(3) The adaptive threshold processor may further convert to 0 all velocity values of the second velocity value data V2 corresponding to coordinates of observation points associated with power values of the first power value data P1(X,Y) that are equal to or less than the power value threshold Pth, in order to generate the third velocity value data V3.

According to this configuration, for example, it is possible to adaptively remove from the second velocity value data V2 a clutter component caused by noise, by detecting the first power value data P1 having a small signal intensity, and it is possible to improve Doppler image quality by accurate extraction of a blood flow component.

Further, the adaptive threshold processor may generate the second power value data P2 by removing power values from the first power value data P1 that are equal to or less than the power value threshold Pth, and the image generator may generate power Doppler image data based on the second power value data P2.

According to this configuration, for example, it is possible to adaptively remove from the power Doppler signal a clutter component caused by noise, by detecting the first power value data P1 having a small signal intensity, and it is possible to improve power Doppler image quality.

Further, the adaptive threshold processor may generate the third velocity value data V3 by calculating a coefficient applicable to data in which the velocity values of the second velocity value data V2 have an absolute value equal to or loss than the velocity threshold Vth, and multiplying the second velocity value data V2 by the coefficient.

According to this configuration, it is possible to eliminate processing summing the third velocity value data V3 with absolute values of the tissue velocity value data Vt. Thus, in addition to adaptively removing a clutter component from a Doppler signal by detecting the tissue velocity Vt based on a Doppler signal, it is possible to reduce calculation and a processor load.

Further, the tissue velocity detector may further calculate tissue power value data Pt by calculating a power value for each set of coordinates of the observation points, and the adaptive threshold processor may, when generating the third velocity value data V3, further convert to 0 velocity values of the second velocity value data V2 corresponding to coordinates of observation points associated with power values of the tissue power value data that are equal to or less than a tissue power value threshold.

According to this configuration, it is possible to eliminate processing summing the third velocity value data V3 with absolute values of the tissue power value data Pt. Thus, it is possible to adaptively remove a clutter component from a power Doppler signal by detecting the tissue velocity Vt and power Pt based on a Doppler signal, and in addition to improving power Doppler image quality by accurate extraction of a blood flow component, it is possible to reduce calculation and a processor load.

(4) The present disclosure describes the embodiments above, but the present disclosure is not limited to these embodiments, and the following examples are also included in the scope of the present invention.

For example, the present invention may be a computer system including a microprocessor and a memory, the memory storing a computer program and the microprocessor operating according to the computer program. For example, the present invention may be a computer system that operates (or instructs operation of connected elements) according to a computer program of a diagnostic method of an ultrasound diagnostic device of the present invention.

Further, examples in which all or part of the ultrasound diagnostic device, or all or part of a beamforming section are constituted by a computer system including a microprocessor, a storage medium such as ROM, RAM, etc., a hard disk unit, and the like, are included in the present invention. A computer program for achieving the same operations as the devices described above may be stored in RAM or a hard disk unit; the microprocessor operating according to the computer program, thereby realizing the functions of each device.

Further, all or part of the elements of each device may be configured as one system large scale integration (LSI). A system LSI is an ultra-multifunctional LSI manufactured by integrating a plurality of elements on one chip, and more specifically is a computer system including a microprocessor, ROM, RAM, and the like. The plurality of elements can be integrated on one chip, or a portion may be integrated on one chip. Here, LSI may refer to an integrated circuit, a system LSI, a super LSI, or an ultra LSI, depending on the level of integration. A computer program for achieving the same operation as the devices described above may be stored in the RAM. The microprocessor operates according to the computer program, the system LSI thereby realizing the functions. For example, a case of the beamforming method of the present invention stored as a program of an LSI, the LSI inserted into a computer, and a defined program (beamforming method) being executed is also included in the present invention.

Note that methods of circuit integration are not limited to LSI, and implementation may be achieved by a dedicated circuit or general-purpose processor. After LSI manufacture, a field programmable gate array (FPGA) or a reconfigurable processor, in which circuit cell connections and settings in the LSI can be reconfigured, may be used.

Further, if a circuit integration technology is introduced that replaces LSI due to advances in semiconductor technology or another derivative technology, such technology may of course be used to integrate the function blocks.

Further, all or part of the functions of an ultrasonic diagnostic device pertaining to at least one embodiment may be implemented by execution of a program by a processor such as a CPU. The present invention may be a non-transitory computer-readable storage medium on which a program is stored that causes execution of an MTI filter or velocity analysis of an ultrasound diagnostic device described above. A program and signals may be recorded and transferred on a storage medium so that the program may be executed by another independent computer system, or the program may of course be distributed via a transmission medium such as the Internet.

Alternatively, each component element of an ultrasound diagnostic device pertaining to an embodiment may be implemented by a programmable device such as a central processing unit (CPU), a graphics processing unit (GPU), a processor, or the like, and software. The case of implementation using a GPU refers to general purpose computing on a graphics processing unit (GPGPU). These component elements can each be a single circuit component or an assembly of circuit components. Further, a plurality of component elements can be combined into a single circuit component or can be an aggregate of a plurality of circuit components.

According to an ultrasound diagnostic device pertaining to at least one embodiment, the ultrasound diagnostic device includes a data storage as a storage device. However, the storage device is not limited to this example and a semiconductor memory, hard disk drive, optical disk drive, magnetic storage device, or the like may be externally connectable to the ultrasound diagnostic device.

Further, the division of function blocks in the block diagrams is merely an example, and a plurality of function blocks may be implemented as one function block, one function block may be divided into a plurality, and a portion of a function may be transferred to another function block. Further, a single hardware or software element may process the functions of a plurality of function blocks having similar functions in parallel or by time division.

Further, the order in which steps described above are executed is for illustrative purposes, and the steps may be in an order other than described above. Further, a portion of the steps described above may be executed simultaneously (in parallel) with another step.

Further, the ultrasound diagnostic device is described as having an externally connected probe and display, but may be configured with an integral probe and/or display.

Further, according to at least one embodiment, a probe configuration is illustrated in which a plurality of piezoelectric elements are arranged along a one-dimensional direction. However, probe configuration is not limited to this. For example, a two-dimensional transducer array in which a plurality of piezoelectric transducers are arrayed on a two-dimensional plane or a rocking-type probe that acquires a three-dimensional tomographic image by mechanical rocking of a plurality of transducers arranged along a one-dimensional direction may be used as appropriate, depending on measurement requirements. For example, when a probe with a two-dimensional array is used, irradiation position and direction of a transmitted ultrasound beam can be controlled by changes to timing of voltage application and voltage value applied to individual piezoelectric transducers.

Further, a portion of functions of transmitters and receivers may be included in the probe. For example, a transmission electrical signal may be generated and converted to ultrasound in the probe, based on a control signal for generating a transmission electrical signal outputted from the transmitter. It is possible to use a configuration that converts received reflected ultrasound into a reception electrical signal and generates a reception signal based on the reception electrical signal in the probe.

Further, at least a portion of functions of each ultrasound diagnostic device pertaining to an embodiment, and each modification thereof, may be combined. Further, the numbers used above are all illustrative, for the purpose of explaining the present invention in detail, and the present invention is not limited to the example numbers used above.

Further, the present invention includes various modifications that are within the scope of conceivable ideas by a person skilled in the art.

<<Review>>

An ultrasound signal processing device pertaining to an embodiment of the present disclosure is an ultrasound signal processing device that calculates blood flow information by driving a plurality of transducers arranged in an ultrasound probe to execute ultrasound transmission and reception with respect to a subject, the ultrasound signal processing device including ultrasound signal processing circuitry, the ultrasound signal processing circuitry comprising: a transmitter that transmits, a plurality of times, via the plurality of transducers, detection waves to a region of interest denoting a range to be analyzed in the subject; a reception beamformer that generates, for each of the detection waves, a reception signal sequence based on reflected ultrasound from the subject received in a time sequence by the plurality of transducers; a quadrature detector that generates, for each of the detection waves, a first complex Doppler signal sequence through quadrature detection of the reception signal sequence; a tissue velocity detector that generates tissue velocity value data by calculating velocity values for each set of coordinates of observation points in the region of interest from the first complex Doppler signal sequence, a filter processor that generates a second complex Doppler signal sequence by performing clutter removal filter processing on the first complex Doppler signal sequence; a blood flow calculator that generates first velocity value data by calculating velocity values for each set of coordinates of the observation points from the second complex Doppler signal sequence; an adaptable threshold processor that generates, for each set of coordinates of the observation points, (i) second velocity value data based on the first velocity value data and the tissue velocity value data, and (ii) third velocity value data by applying a correction to velocity values of the second velocity value data that have an absolute value equal to or less than a velocity threshold; and an image generator that generates, for each set of coordinates of the observation points, color Doppler image data based on the third velocity value data.

According to this configuration, velocity of tissue can be detected based on Doppler signals and a clutter component caused by tissue movement can be adaptively removed from the Doppler signals. This makes it possible to extract the blood flow component with high accuracy while reliably removing the clutter component. Thus, the blood flow component can be extracted with high accuracy and Doppler image quality can be improved.

Further, according to this configuration, a clutter component is detected from a signal from the same transmission and reception sequence as the Doppler signal to be corrected, and where the clutter signal exists in the same range as the Doppler signal, adaptive correction is performed according to size of the clutter component, and therefore Doppler image quality is improved when compared with a conventional clutter removal method in which transmission and reception sequences are different for acquisition of a signal used to determine a correction value and acquisition of a signal to be corrected.

According to at least one embodiment, the tissue velocity detector further generates, for each set of coordinates of the observation points, fourth velocity value data by summing the third velocity value data and the tissue velocity value data, and the image generator generates the color Doppler image data based on the fourth velocity value data.

According to this configuration, after removing the clutter component by adaptive threshold processing from the first velocity value data from which the tissue velocity value data is subtracted by the subtractor 10552, the result is summed with the tissue velocity value data, returning the signal to its original state based on tissue velocity.

According to at least one embodiment, the adaptive threshold processor generates the second velocity value data by subtracting values based on the tissue velocity value data from the first velocity value data. According to at least one embodiment, the values the adaptive threshold processor subtracts from the first velocity value data to generate the second velocity value data are the products of multiplication of the tissue velocity data by correction coefficients. According to at least one embodiment, the adaptive threshold processor generates the third velocity value data by subtracting velocity value data of absolute value equal to or less than a velocity threshold from the second velocity value data.

According to this configuration, an ultrasound signal processing device can be implemented that detects velocity of tissue based on Doppler signals in order to adaptively remove a clutter component from the Doppler signals.

According to at least one embodiment, the adaptive threshold processor, when generating the third velocity value data, further converts to 0 velocity values of the second velocity value data corresponding to coordinates of observation points associated with power values of first power value data that are equal to or less than a power value threshold.

According to this configuration, for example, it is possible to adaptively remove from the second velocity value data a clutter component caused by noise, by detecting the first power value data having a small signal intensity, and it is possible to improve Doppler image quality by accurate extraction of a blood flow component.

According to at least one embodiment the blood flow calculator further generates first power value data by calculating a power value for each set of coordinates of the observation points from the second complex Doppler signal sequence, the adaptive threshold processor further generates second power value data by removing from the first power value data power values that are equal to or less than a power value threshold, and the image generator further generates power Doppler image data based on the second power value data.

According to this configuration, for example, it is possible to adaptively remove from the power Doppler signal a clutter component caused by noise, by detecting the first power value data having a small signal intensity, and it is possible to improve power Doppler image quality by accurate extraction of a blood flow component.

According to at least one embodiment, the adaptive threshold processor generates the third velocity value data by calculating a coefficient applicable to data in which the velocity values of the second velocity value data have an absolute value equal to or less than the velocity threshold, and multiplying the second velocity value data by the coefficient.

According to this configuration, it is possible to eliminate processing summing the third velocity value data with absolute values of the tissue velocity value data. Thus, in addition to adaptively removing a clutter component from a Doppler signal by detecting the tissue velocity based on a Doppler signal, it is possible to reduce calculation and a processor load, leading to faster processing.

According to at least one embodiment the blood flow calculator further generates first power value data by calculating a power value for each set of coordinates of the observation points from the second complex Doppler signal sequence, the adaptive threshold processor generates second power value data by calculating a coefficient applicable to data in which the velocity values of the second velocity value data have an absolute value equal to or less than a velocity value threshold, and multiplying the first power value data by the coefficient, and the image generator further generates power Doppler image data based on the second power value data.

According to at least one embodiment, the tissue velocity detector further calculates tissue power value data by calculating a power value for each set of coordinates of the observation points, and the adaptive threshold processor, when generating the third velocity value data, further converts to 0 velocity values of the second velocity value data corresponding to coordinates of observation points associated with power values of the tissue power value data that are equal to or less than a tissue power value threshold.

According to these configurations, it is possible to eliminate processing summing the third velocity value data with absolute values of the tissue velocity value data. Thus, it is possible to adaptively remove a clutter component from a power Doppler signal by detecting the tissue velocity and power based on a Doppler signal, and in addition to improving power Doppler image quality by accurate extraction of a blood flow component, it is possible to reduce calculation and a processor load, leading to faster processing.

Further, an ultrasound diagnostic device pertaining to at least one embodiment comprises the ultrasound signal processing device according to any one embodiment; and the ultrasound probe.

According to this configuration, an ultrasound diagnostic device can be implemented that extracts a blood flow component with high accuracy to improve Doppler image quality.

Further, an ultrasound signal processing device according to at least one embodiment is an ultrasound signal processing device that calculates blood flow information by driving a plurality of transducers arranged in an ultrasound probe to execute ultrasound transmission and reception with respect to a subject, the ultrasound signal processing device including ultrasound signal processing circuitry, the ultrasound signal processing circuitry comprising: a transmitter that transmits, a plurality of times, via the plurality of transducers, detection waves to a region of interest denoting a range to be analyzed in the subject; a reception beamformer that generates, for each of the detection waves, a reception signal sequence based on reflected ultrasound from the subject received in a time sequence by the plurality of transducers; a quadrature detector that generates, for each of the detection waves, a first complex Doppler signal sequence through quadrature detection of the reception signal sequence; a tissue velocity detector that generates tissue velocity value data by calculating velocity values for each set of coordinates of observation points in the region of interest from the first complex Doppler signal sequence; a filter processor that generates a second complex Doppler signal sequence by performing clutter removal filter processing on the first complex Doppler signal sequence; a blood flow calculator that generates, from the second complex Doppler signal sequence, first velocity value data by calculating velocity values for each set of coordinates of the observation points and first power value data by calculating power values for each set of coordinates of the observation points; an adaptable threshold processor that generates, for each set of coordinates of the observation points, (i) second velocity value data based on the first velocity value data and the tissue velocity value data, and (ii) second power value data by calculating a coefficient applicable to data in which the velocity values of the second velocity value data have an absolute value equal to or less than a velocity threshold, and multiplying the first power value data by the coefficient; and an image generator that generates power Doppler image data based on the second power value data.

Further, an ultrasound signal processing method according to at least one embodiment is an ultrasound signal processing method that calculates blood flow information by driving a plurality of transducers arranged in an ultrasound probe to execute ultrasound transmission and reception with respect to a subject, the ultrasound signal processing method comprising: transmitting, a plurality of times, via the plurality of transducers, detection waves to a region of interest denoting a range to be analyzed in the subject; generating, for each of the detection waves, a reception signal sequence based on reflected ultrasound from the subject received in a time sequence by the plurality of transducers; performing quadrature detection that generates, for each of the detection waves, a first complex Doppler signal sequence through quadrature detection of the reception signal sequence; generating tissue velocity value data by calculating velocity values for each set of coordinates of observation points in the region of interest from the first complex Doppler signal sequence; generating a second complex Doppler signal sequence by performing clutter removal filter processing on the first complex Doppler signal sequence; generating first velocity value data by calculating velocity values for each set of coordinates of the observation points from the second complex Doppler signal sequence; generating, for each set of coordinates of the observation points, (i) second velocity value data based on the first velocity value data and the tissue velocity value data, and (ii) third velocity value data by applying a correction to velocity values of the second velocity value data that have an absolute value equal to or less than a velocity threshold; and generating, for each set of coordinates of the observation points, color Doppler image data based on the third velocity value data.

According to this configuration, velocity of tissue can be detected based on Doppler signals and a clutter component caused by tissue movement can be adaptively removed front the Doppler signals, and therefore it is possible to extract a blood flow component with high accuracy while reliably removing the clutter component.

Although the technology pertaining to the present disclosure has been fully described by way of examples with reference to the accompanying drawings, various changes and modifications will be apparent to those skilled in the art. Therefore, unless such changes and modifications depart from the scope of the present disclosure, they should be construed as being included therein.

What is claimed is:

1. An ultrasound signal processing device that calculates blood flow information by driving a plurality of transducers arranged in an ultrasound probe to execute ultrasound transmission and reception with respect to a subject, the ultrasound signal processing device including ultrasound signal processing circuitry, the ultrasound signal processing circuitry comprising:
   a transmitter that transmits, a plurality of times, via the plurality of transducers, detection waves to a region of interest denoting a range to be analyzed in the subject;
   a reception beamformer that generates, for each of the detection waves, a reception signal sequence based on reflected ultrasound from the subject received in a time sequence by the plurality of transducers;
   a quadrature detector that generates, for each of the detection waves, a first complex Doppler signal sequence through quadrature detection of the reception signal sequence;
   a tissue velocity detector that generates tissue velocity value data by calculating velocity values for each set of coordinates of observation points in the region of interest from the first complex Doppler signal sequence;
   a filter processor that generates a second complex Doppler signal sequence by performing clutter removal filter processing on the first complex Doppler signal sequence;
   a blood flow calculator that generates first velocity value data by calculating velocity values for each set of coordinates of the observation points from the second complex Doppler signal sequence;
   an adaptable threshold processor that generates, for each set of coordinates of the observation points, (i) second velocity value data based on the first velocity value data and the tissue velocity value data, and (ii) third velocity value data by applying a correction to velocity values of the second velocity value data that have an absolute value equal to or less than a velocity threshold,
   wherein the tissue velocity detector further generates, for each set of coordinates of the observation points, fourth velocity value data by summing the third velocity value data and the tissue velocity value data; and
   an image generator that generates, for each set of coordinates of the observation points, color Doppler image data based on the fourth velocity value data.

2. The ultrasound signal processing device of claim 1, wherein
   the adaptive threshold processor generates the second velocity value data by subtracting values based on the tissue velocity value data from the first velocity value data.

3. The ultrasound signal processing device of claim 2, wherein
   the values that are subtracted from the first velocity value data to generate the second velocity value data are the products of multiplication of the tissue velocity data by correction coefficients.

4. The ultrasound signal processing device of claim 1, wherein
   the correction applied by the adaptive threshold processor is a removal of to the velocity values of the second velocity value data that have an absolute value equal to or less than the velocity threshold.

5. The ultrasound signal processing device of claim 1, wherein
   the adaptive threshold processor, when generating the third velocity value data, further converts to 0 velocity values of the second velocity value data corresponding to coordinates of observation points associated with power values of first power value data that are equal to or less than a power value threshold.

6. The ultrasound signal processing device of claim 1, wherein
   the blood flow calculator further generates first power value data by calculating a power value for each set of coordinates of the observation points from the second complex Doppler signal sequence,
   the adaptive threshold processor further generates second power value data by removing from the first power value data power values that are equal to or less than a power value threshold, and
   the image generator further generates power Doppler image data based on the second power value data.

7. The ultrasound signal processing device of claim 1, wherein
   the adaptive threshold processor generates the third velocity value data by calculating a coefficient applicable to data in which the velocity values of the second velocity value data have an absolute value equal to or less than the velocity threshold, and multiplying the second velocity value data by the coefficient.

8. The ultrasound signal processing device of claim 1, wherein
   the blood flow calculator further generates first power value data by calculating a power value for each set of coordinates of the observation points from the second complex Doppler signal sequence,
   the adaptive threshold processor generates second power value data by calculating a coefficient applicable to data in which the velocity values of the second velocity value data have an absolute value equal to or less than a velocity value threshold, and multiplying the first power value data by the coefficient, and
   the image generator further generates power Doppler image data based on the second power value data.

9. The ultrasound signal processing device of claim 1, wherein the tissue velocity detector further calculates tissue power value data by calculating a power value for each set of coordinates of the observation points;

the adaptive threshold processor, when generating the third velocity value data, further converts to 0 velocity values of the second velocity value data corresponding to coordinates of observation points associated with power values of the tissue power value data that are equal to or less than a tissue power value threshold.

10. The ultrasound diagnostic processing device of claim 1, further comprising:
an ultrasound probe connected to the transmitter and the reception beamformer.

11. An ultrasound signal processing method that calculates blood flow information by driving a plurality of transducers arranged in an ultrasound probe to execute ultrasound transmission and reception with respect to a subject, the ultrasound signal processing method comprising:

transmitting, a plurality of times, via the plurality of transducers, detection waves to a region of interest denoting a range to be analyzed in the subject;

generating, for each of the detection waves, a reception signal sequence based on reflected ultrasound from the subject received in a time sequence by the plurality of transducers;

performing quadrature detection that generates, for each of the detection waves, a first complex Doppler signal sequence through quadrature detection of the reception signal sequence;

generating tissue velocity value data by calculating velocity values for each set of coordinates of observation points in the region of interest from the first complex Doppler signal sequence;

generating a second complex Doppler signal sequence by performing clutter removal filter processing on the first complex Doppler signal sequence;

generating first velocity value data by calculating velocity values for each set of coordinates of the observation points from the second complex Doppler signal sequence;

generating, for each set of coordinates of the observation points, (i) second velocity value data based on the first velocity value data and the tissue velocity value data, and (ii) third velocity value data by applying a correction to velocity values of the second velocity value data that have an absolute value equal to or less than a velocity threshold, generating, for each set of coordinates of the observation points, fourth velocity value data by summing the third velocity value data and the tissue velocity value data; and generating, for each set of coordinates of the observation points, color Doppler image data based on the fourth velocity value data.

12. An ultrasound signal processing device that calculates blood flow information by driving a plurality of transducers arranged in an ultrasound probe to execute ultrasound transmission and reception with respect to a subject, the ultrasound signal processing device including ultrasound signal processing circuitry, the ultrasound signal processing circuitry comprising:
a transmitter that transmits, a plurality of times, via the plurality of transducers, detection waves to a region of interest denoting a range to be analyzed in the subject;

a reception beamformer that generates, for each of the detection waves, a reception signal sequence based on reflected ultrasound from the subject received in a time sequence by the plurality of transducers;

a quadrature detector that generates, for each of the detection waves, a first complex Doppler signal sequence through quadrature detection of the reception signal sequence;

a tissue velocity detector that generates tissue velocity value data by calculating velocity values for each set of coordinates of observation points in the region of interest from the first complex Doppler signal sequence;

a filter processor that generates a second complex Doppler signal sequence by performing clutter removal filter processing on the first complex Doppler signal sequence;

a blood flow calculator that generates, from the second complex Doppler signal sequence, first velocity value data by calculating velocity values for each set of coordinates of the observation points and first power value data by calculating power values for each set of coordinates of the observation points;

an adaptable threshold processor that generates, for each set of coordinates of the observation points, (i) second velocity value data based on the first velocity value data and the tissue velocity value data, and (ii) second power value data by calculating a coefficient applicable to data in which the velocity values of the second velocity value data have an absolute value equal to or less than a velocity threshold, and multiplying the first power value data by the coefficient; and an image generator that generates power Doppler image data based on the second power value data.

* * * * *